United States Patent
Lowe et al.

(10) Patent No.: US 12,011,272 B2
(45) Date of Patent: Jun. 18, 2024

(54) PROCESS OF CAPTURING A BIOPOTENTIAL SIGNAL AT A SURFACE OF A BODY AND APPARATUS THEREFOR

(71) Applicant: AUCKLAND UNIVERSITY OF TECHNOLOGY (AUT), Auckland (NZ)

(72) Inventors: Andrew Lowe, Auckland (NZ); Anubha Kalra, Auckland (NZ); Gautam Anand, Auckland (NZ); Raymond Simpkin, Auckland (NZ)

( * ) Notice: Subject to any disclaimer, the term of this patent is extended or adjusted under 35 U.S.C. 154(b) by 0 days.

(21) Appl. No.: 17/609,939

(22) PCT Filed: May 11, 2020

(86) PCT No.: PCT/NZ2020/050049
§ 371 (c)(1),
(2) Date: Nov. 9, 2021

(87) PCT Pub. No.: WO2020/226515
PCT Pub. Date: Nov. 12, 2020

(65) Prior Publication Data
US 2022/0202336 A1  Jun. 30, 2022

(30) Foreign Application Priority Data

May 9, 2019  (AU) .................................. 2019901584

(51) Int. Cl.
*A61B 5/302* (2021.01)
*A61B 5/00* (2006.01)
(Continued)

(52) U.S. Cl.
CPC ............. *A61B 5/302* (2021.01); *A61B 5/053* (2013.01); *A61B 5/308* (2021.01); *A61B 5/327* (2021.01);
(Continued)

(58) Field of Classification Search
None
See application file for complete search history.

(56) References Cited

U.S. PATENT DOCUMENTS 3,730,171 A * 5/1973 Namon ................ A61B 5/0535
600/526
3,841,314 A * 10/1974 Page .................. A61B 5/02255
600/479

(Continued)

FOREIGN PATENT DOCUMENTS

WO  2015061282 A1  4/2015

OTHER PUBLICATIONS

H. Su et al., "A non-contact biopotential sensing system with motion artifact suppression," 2013 International Conference on Communications, Circuits and Systems (ICCCAS), Chengdu, 2013, pp. 314-318.

(Continued)

*Primary Examiner* — Kennedy Schaetzle
(74) *Attorney, Agent, or Firm* — PCFB, LLC; Justin K. Flanagan

(57) ABSTRACT

In one embodiment the invention provides a process of capturing a biopotential signal at a surface of a body using a sensor receiver which forms a first signal connection the body wherein one or more parameters of impedance of the first signal connection are unknown. The process comprises receiving the biopotential signal at an output of a first signal channel having a first transfer function which is dependent on the one of more unknown first impedance parameters. The process also comprises receiving the biopotential signal at an output of a second signal channel having a second transfer function dependent on the one of more unknown first impedance parameters. The process also comprises deriving a set of relations for the biopotential signal. The set of relations is defined dependent on the transfer function of (Continued)

the first signal channel, the transfer function of the second signal channel, and outputs of the first and second signal channels; and solving the set of relations to determine the captured biopotential signal.

22 Claims, 9 Drawing Sheets

(51) Int. Cl.
    *A61B 5/053*     (2021.01)
    *A61B 5/308*     (2021.01)
    *A61B 5/327*     (2021.01)
    *G01R 27/02*     (2006.01)
    *G06F 17/16*     (2006.01)
    *A61B 5/277*     (2021.01)

(52) U.S. Cl.
    CPC ............ *A61B 5/6813* (2013.01); *G01R 27/02* (2013.01); *G06F 17/16* (2013.01); *A61B 5/277* (2021.01)

(56) References Cited

U.S. PATENT DOCUMENTS

| | | |
|---|---|---|
| 9,603,542 B2 | 3/2017 | Veen |
| 2007/0167858 A1 | 7/2007 | Virtanen |
| 2017/0188830 A1 | 7/2017 | Sankai |
| 2019/0015011 A1 | 1/2019 | Kim |

OTHER PUBLICATIONS

International Preliminary Report on Patentability, PCT/NZ2020/050049, dated Jul. 1, 2021.

\* cited by examiner

PROCESS OF CAPTURING A BIOPOTENTIAL SIGNAL AT A SURFACE OF A BODY AND APPARATUS THEREFOR

FIELD OF THE INVENTION

This invention relates to improvements in respect of sensing biopotential signals, such as sensing biopotential signals at the surface of a body or, more specifically, sensing biopotential signals at the skin of a body.

BACKGROUND OF THE INVENTION

In various applications it is desirable to sense and/or measure potential signals of a body. In some applications the potential signal is a biological potential signal, or biopotential signal. In some applications a potential signal may be a voltage potential signal. In various applications the potential signal may need to be sensed at the surface of the body. In some applications the body is a human or animal body.

In various applications it is desirable to sense biopotential signals non-invasively. This may involve sensing the biopotential signal at the surface of a body.

One common application for sensing potential signals at the surface of a body is Electrocardiography. Electrocardiography (ECG or EKG) is the process of recording the electrical activity of the heart over a period of time using electrodes placed at the skin of the body of a subject. These electrodes detect a biopotential signal in the form of small electrical changes on the skin that arise from the heart muscle's electrophysiologic pattern of depolarizing and repolarizing during each heartbeat.

Conventionally the ECG electrodes are electrically connected to the skin to receive this ECG signal. These conventionally involve a sensor receiver with an electrode and an adhesive pad which accommodate conductive gel between an electrode and the skin of the subject.

Various problems arise with conventional electrical connection for ECG signals, or other biopotential signals.

Some of these problems arise from the nature of skin as an organ of a biological body.

Various problems arise in the use of a conductive gel.

Particular problems arise in longevity of the connection to skin for sensing biopotential signals. Particular problems arise in the electrical properties of conventional sensor receivers.

Some conventional devices are known which sense a biopotential signal using a capacitive coupling between a body and an electrode.

A problem that arises with some capacitive coupling devices poor signal to noise due to constraints on impedance of the capacitive coupling between a sensor and a body.

Another problem that arises with some capacitive coupling devices is motion-induced artefacts on the captured signal.

Another problem that arises with some capacitive coupling devices is constraints on the capacitive coupling. For example, some devices may rely on the coupling being purely capacitive and able to maintain a charge. In many applications the coupling is not purely capacitive. In some applications there may be a resistive component to the coupling which bleeds away any charge on the electrode relied upon by the device to measure the signal.

It would therefore be of advantage to have a sensor receiver which could address any or all of the above problems, or at least provide the public with an alternative choice.

It would therefore be of advantage to have sensor electronics which could address any or all of the above problems, or at least provide the public with an alternative choice.

DISCLOSURE OF THE INVENTION

In one aspect the invention provides operable to reconstruct a biopotential signal from a signal received at a surface of a body, the apparatus comprising:

a sensor device which forms a first signal connection for the biopotential signal, the first signal connection having a first sensor impedance, and which forms a second signal connection for the biopotential signal, the second signal connection having a second sensor impedance, wherein the sensor device is arranged such that the second sensor impedance is linearly related to the first sensor impedance by an impedance relation;

sensor circuitry which provides i) a first sensor signal related to the biopotential signal by a first channel expression which is dependent on parameter values for the sensing circuitry providing the first sensor signal, dependent on the first sensor impedance and dependent on the biopotential signal, and ii) a second sensor signal related to the biopotential signal by a second channel expression which is dependent on parameter values for the sensing circuitry, dependent on the second sensor impedance dependent on the biopotential signal;

a processor operable to read data carrying information on parameter values of the receiver circuitry, operable to read data carrying information on the first sensor signal, operable to read data carrying information on the second sensor signal and operable to generate data carrying information on a reconstruction of the biopotential signal said generation using a derived relation which is derived from a set of relations comprising the first channel expression, the second channel expression and the impedance relation, wherein the biopotential relation is independent of the first sensor impedance.

A channel expression may define a transfer function for a channel.

The signal connection may be represented in a channel expression as one or more unknown impedance parameters which are eliminated in the derived expression used by the processor. The signal connection may have two or more impedance parameters which are unknown, such as due to properties of skin of the body or spacing between the body and a sensor and/or properties of materials between a sensor and the body and/or properties of a sensor device. For example, a signal connection may be intended to be capacitive only but may have an ohmic parameter which dissipates charge on an electrode of a sensor. The signal connection may have two or more impedance parameters which are variable and unknown at any given time, such as may occur due to motion of the body and/or to a sensor relative to the body or due to effects occurring at the body.

The receiver circuitry may have components selected so the circuitry provides the transfer function defined and/or can be described by the channel expression.

The transfer function of the first channel may comprise an analytic expression for the gain of a first channel comprising at least one of a relation to the current entering the first channel and a relation to the voltage signal at the entry of the first channel.

The transfer function of the second channel may comprise an analytic expression for the gain of a second channel comprising at least one of an expression to the current entering the second channel and a relation to the signal at the entry of the second channel.

The sensor circuitry may provide a first channel and the first channel expression is:

$$V_1 = i_{u1}TF_{1i} + V_{in}TF_{1v} + i_{u1}Z_{u1}TF_{1v}$$

where $i_{u1}$ is the current entering the channel, $V_{in}$ is the signal at the entry of the channel, $V_1$ is the output of the first signal channel, $Z_{u1}$ is the unknown first impedance, $TF_{1i}$ is the relation for the gain relation to the current entering the channel, $TF_{1v}$ is the relation for the gain relation to the signal at the entry of the channel.

The sensor circuitry may provide a second channel and the second channel expression is:

$$V_2 = i_{u2}TF_{2i} + V_{in}TF_{2v} + i_{u2}Z_{u2}TF_{2v}$$

where $i_{u2}$ is the current entering the channel, $V_{in}$ is the signal at the entry of the channel, $V_2$ is the output of the second signal channel, $Z_{u2}$ is the unknown second impedance, $TF_{2i}$ is the relation for the gain relation to the current entering the channel, $TF_{2v}$ is the relation for the gain relation to the signal at the entry of the channel.

The first signal channel may comprise the first signal connection in series with sensor circuitry arranged so that the first channel transfer function is non-linearly related to the first sensor impedance.

The impedance relation may be:

$$Z_{u2} = H_{12}Z_{u1} + K_{12}$$

where $Z_{u2}$ is the second sensor impedance $Z_{u2}$ is the first sensor impedance, $H_{12}$ is a factor and $k_{12}$ is a constant.

The derived expression used by the processor:

$$V_{in} = \frac{H_{12}i_{u2}(-V_1 + i_{u1}TF_{1i})TF_{2v} + i_{u1}TF_{1v}(V_2 - i_{u2}TF_{2i} + i_{u2}k_{12}TF_{2v})}{(i_{u1} - H_{12}i_{u2})TF_{1v}TF_{2v}}.$$

The processor may be operable to generate data carrying information on an estimate of the unknown first impedance using the relation:

$$Z_{u1} = \frac{(-V_1 + i_{u1}TF_{1i})TF_{2v} + TF_{1v}(V_2 - i_{u2}TF_{2i} + i_{u2}k_{12}TF_{2v})}{(i_{u1} - H_{12}i_{u2})TF_{1v}TF_{2v}},$$

wherein $i_{u1}$ is a current entering the first channel and $i_{u2}$ entering the second channel.

The receiver circuitry may be operable to output a first current measurement $i_{u1}$ of a current entering the first channel and a second current measurement $i_{u2}$ entering the second channel.

The circuitry may be arranged so that current entering a signal channel may be related to the output of the signal channel.

The first channel expression may be a transfer function of a first channel and the second channel expression may be a transfer function of a second channel.

The first channel transfer function may comprise an analytic relation for the gain of a first channel comprising an operational amplifier circuit having a selected feedback impedance a selected series impedance connected at an input of an operational amplifier and comprising an impedance connected to the selected series impedance to represent the first sensor impedance.

The second channel transfer function of the second channel may comprise an analytic relation for the gain of a second channel comprising an operational amplifier circuit having a selected feedback impedance a selected series impedance connected at an input of an operational amplifier and comprising an impedance connected to the selected series impedance to represent the second sensor impedance.

The transfer function of the first channel may comprise:

$$V_1 = -\frac{Z_{f1}}{Z_{s1} + Z_{u1}}V_{in}$$

where $Z_{f1}$ is a selected first channel feedback impedance $Z_{s1}$ is a selected first channel series impedance, and the transfer function of the second channel comprises $$V_2 = -\frac{Z_{f2}}{Z_{s2} + H_{12}Z_{u1} + k_{12}}V_{in}$$

where $Z_{f2}$ is a selected second channel feedback impedance $Z_{s2}$ is a selected second channel series impedance, and where the captured biopotential signal is determined from $$V_{in} = -\frac{V_1V_2(k_{12} - H_{12}Z_{s1} + Z_{s2})}{-H_{12}V_2Z_{f1} + V_1Z_{f2}}.$$

The receiver circuitry may comprise a first receiver circuit having a transfer function defined by a first feedback impedance and a first series impedance.

The first receiver circuit may be a charge amplifier.

The charge amplifier may be an inverting amplifier with a feedback impedance between an output and an inverting input and a series impedance at the inverting input.

The biopotential signal, outputs of the receiver circuitry and sensor impedances may be defined in the frequency domain and the processor may operate in the frequency domain.

The signals and parameters $V_{in}$, $V_1$, $V_2$, $H_{12}$, $k_{12}$, $Z_{s1}$, $Z_{s2}$, $Z_{f1}$ and $Z_{f2}$ may be in the frequency domain.

The first channel expression may comprise:

$$V_1 = \left(1 + \frac{Z_{f1}}{Z_1}\right)V_{in}$$

where $Z_1$ is the first sensor impedance and wherein the second channel expression comprises $$V_2 = \left(1 + \frac{Z_{f2}}{Z_2}\right)V_{in}$$

where $Z_2$ is the second sensor impedance where the data carrying information on the reconstructed biopotential signal is generated by the processor using:

$$V_{in} = \frac{V_2Z_2}{Z_2 + Z_{f2}}.$$

The first channel expression may comprise:

$$V_1 = \left(1 + \frac{Z_{f1}}{Z_1}\right)V_{in}$$

where $Z_1$ the first signal impedance signal connection and the transfer function of the second channel comprises $$V_2 = \left(1 + \frac{Z_{f2}}{Z_2}\right)V_{in}$$

where $Z_2$ is the second impedance signal and where the derived expression is $$V_{in} = \frac{i_{u1}V_2 Z_2(Z_1 + Z_{f1}) - H_{12}i_{u2}V_1 Z_1(Z_2 + Z_{f2})}{(i_{u1} - H_{12}i_{u2})(Z_1 + Z_{f1})(Z_2 + Z_{f2})}$$

where $i_{u1}$ is the current entering the first input channel and $i_{u2}$ is the current entering the second input channel.

The first channel expression may comprise:

$$V_1 = \frac{Z_{41}}{Z_{21} + Z_{41}} \frac{(Z_{11} + Z_{31})}{Z_{11}} V_{in}$$

where $Z_{11}, Z_{21}, Z_{31}$ and $Z_{41}$ are impedance parameters of the first signal channel, and the second channel expression may comprise $$V_2 = \frac{Z_{42}}{Z_{22} + Z_{42}} \frac{(Z_{12} + Z_{32})}{Z_{12}} V_{in}$$

where $Z_{12}, Z_{22}, Z_{32}$ and $Z_{42}$ are impedance parameters of the first signal channel, and where the captured biopotential signal may be determined from $$V_{in} = \frac{V_1 V_2 Z_{11} Z_{12}(Z_{22} - H_{12}(Z_{21} + Z_{41}) + Z_{42})}{\begin{array}{c}-H_{12}V_2 Z_{12}(Z_{11} + Z_{31})Z_{41} + \\ V_1 Z_{11}(Z_{12} + Z_{32})Z_{42}\end{array}}.$$

The transfer function of each of a multiplicity of n signal channels may comprise:

$$V_n = i_{un}TF_{ni} + V_{in}TF_{nv} + i_{un}Z_{un}TF_{nv}$$

and the relation between the unknown first impedance parameter and unknown second impedance parameter may comprise $$Z_{un} = H_{1n}Z_{u1}$$

and the captured biopotential signal may determined by the processor using $$\begin{pmatrix} V_{in} \\ Z_{u1} \end{pmatrix} = \begin{pmatrix} TF_{1v} & -i_{u1}TF_{1v} \\ TF_{2v} & -H_{12}i_{u2}TF_{2v} \\ \vdots & \vdots \\ TF_{nv} & -H_{1n}i_{un}TF_{nv} \end{pmatrix}^+ \begin{pmatrix} V_1 - i_{u1}TF_{1i} \\ V_2 - i_{u2}TF_{2i} + i_{u2}k_{12}TF_{2v} \\ \vdots \\ V_n - i_{un}TF_{2i} + i_{un}k_{1n}TF_{nv} \end{pmatrix}$$

where $A^+$ represents an operator such that if $Ax=b$, $x=A^+b$ where $Z_{u2}$ is the second sensor impedance $Z_{u2}$ is the first sensor impedance, $H_{12}$ is a factor and $k_{12}$ is a constant, and where $TF_{nv}$ a transfer function.

An another aspect the invention provides a process of capturing a biopotential signal at a surface of a body using a sensor receiver which forms a first signal connection with the body wherein one or more parameters of impedance of the first signal connection are unknown, the process comprising:

receiving the biopotential signal at an output of a first signal channel having a first channel transfer function which is dependent on the one or more unknown first impedance parameters;

receiving the biopotential signal at an output of one or more second signal channels each having a second channel transfer function dependent on the one or more unknown first impedance parameters;

solving a set of relations to determine the captured biopotential signal wherein the set of relations is defined dependent on:

i) the first channel transfer function,
ii) the second channel transfer function, and
iv) outputs of the first and second signal channels.

The second channel transfer function may be dependent on the first unknown impedance parameter by being dependent on a second impedance parameter which has a known relation to the unknown first impedance parameter.

The unknown one or more parameters of impedance of the first signal connection may be the impedance of the first signal connection, and the unknown one or more parameters of impedance of the first signal connection may be the impedance of the first signal connection, and the set of relations may be solved to eliminate the first and second unknown impedance parameters to allow the biopotential signal to be determined independently of the impedance of the first or second signal connections.

The known relation of the unknown second impedance parameter to the unknown first impedance parameter may be an approximation.

The solved set of relations may comprise a first relation which relates the biopotential signal to an expression which is dependent on the output signal of the first signal channel, the unknown first impedance parameter and one or more known parameters for components included in the first signal channel.

The solved set of relations may comprise a second relation which relates the biopotential signal to an expression which is dependent on the output signal of the second signal channel, an unknown second impedance parameter and one or more known parameters for components included in the second signal channel.

The unknown second impedance and one or more known parameters for components included in the second signal channel may be selected such that the second relation does not reduce to the first relation.

The derived set of equations comprises a third relation which relates the unknown second impedance parameter to unknown first impedance parameter.

The first signal channel may be arranged to have a transfer function which is non-linear with respect to the unknown first impedance parameter.

The second signal channel may be arranged to have a transfer function which is non-linear with respect to the unknown first impedance parameter.

In another aspect the invention provides a process for reconstructing a biopotential signal from first and second sensing signals output by sensing circuitry which receives first and second electrode signals from first and second sensor electrodes which each form a connection for the biopotential signal, wherein the second sensor electrode is adapted to provide a signal connection with an impedance which differs from the signal connection of the first electrode by a linear relationship, the process comprising the steps of:
reading first and second sensor signals;
reading data carrying information which defines an expression for the biopotential signal, the expression derived from
i) a first channel expression for the first sensor signal dependent on parameter values for the sensing circuitry providing the first sensor signal, dependent on the impedance formed by the first electrode and dependent on the biopotential signal, and
ii) a second channel expression for the second sensor signal dependent on parameter values for the sensing circuitry providing the second sensor signal, dependent on the impedance formed by the second electrode and dependent on the biopotential signal, and
iii) an expression for the impedance formed by the second electrode dependent on the impedance formed by the first electrode,
wherein said expression for the biopotential signal is derived to eliminate the impedance formed by the first electrode and eliminate the impedance formed by the second electrode; and
determining the bio-potential signal using said expression for the biopotential signal to reconstruct the biopotential signal independently of the first and second impedance.

In another aspect the invention provides a sensing device for sensing biopotential signals in a sensing region at a surface of a body, the sensing device comprising:
first and second input terminals for connection to first and second sensor receivers which each connect the biopotential received at the surface of the body to a respective receiver terminal, wherein a second sensor receiver has a second receiver impedance for the biopotential signal which has a defined relationship with a first receiver impedance of the first receiver;
sensing circuitry operable to connect to first and second receivers to receive first and second receiver signals and to apply a defined transfer function to the first and second receiver signals to output first and second sensing signals; and
a sensing processor operable to determine the biopotential signal dependent on the first and second sensing signals, dependent on parameters of the defined transfer function and dependent on the defined relationship of the first and second receiver impedances.

The defined relationship between the first and second receiver impedances may be substantially linear.

The sensor receiver may comprise one or more electrodes operable to provide a capacitive connection for the biopotential signal at the surface of the body.

The sensor receiver may comprise one or more electrodes operable to provide a conductive connection for the biopotential signal at the surface of the body.

The first and second sensor receivers may comprise respective first and second electrodes each providing a connection for the biopotential signal.

The first and second sensor receivers may have an electrode common to both receivers.

In another aspect of the present invention provides a sensor operable to receive a potential signal in a sensing region at a surface of a body the sensor receiver having a first electrode and a second electrode to form first and second sensing connections in the sensing region to receive the potential signal wherein the electrodes are arranged such that the second connection has an impedance which approximately relates an impedance of the first connection by a defined expression.

The defined expression may be a factor.

In another aspect the invention provides a sensor operable to receive a potential signal in a sensing region at a surface of a body the sensor receiver operable to receive the biopotential signal in the sensing region, wherein the sensor comprises first and second signal pathways to first and second receiver terminals to provide the biopotential signal received to sensing electronics wherein second connection has an impedance which approximately relates an impedance of the first connection by a defined relation.

In another aspect the invention provides a sensor circuitry for a potential signal received by a sensor electrode over an unknown and/or variable impedance, the sensor circuitry comprising first and second output channels for first and second output signals each signal comprising an amplification of the potential signal wherein the amplification is defined by the gain of an operational amplifier with a feedback impedance and with an input impedance wherein the input impedance is comprised of said unknown and/or variable impedance and a series impedance between the sensor electrode and the operational amplifier.

In another aspect the invention provides a process for reconstructing a biopotential signal from a first and second sensing signals output by sensing circuitry which receives first and second electrode signals from first and second sensor electrodes which each form a connection for the biopotential signal, the process comprising the steps of:
reading first and second sensor signals;
reading data carrying information on a relationship between a first sensor impedance formed by the first electrode and a second sensor impedance formed by the electrode;
reading data carrying information on expressions for the biopotential signal independent of the first and second impedance;
determining the bio-potential signals dependent on the first and second sensor signals, on parameter values for the sensing circuitry and dependent on the relationship between the second sensor impedance and first sensor impedance.

BRIEF DESCRIPTION OF THE DRAWINGS

Additional and further aspects of the present invention will be apparent to the reader from the following description of embodiments, given in by way of example only, with reference to the accompanying drawings in which.

Further aspects of the invention will become apparent from the following description of the invention which is given by way of example only of particular embodiments.

BEST MODES FOR CARRYING OUT THE INVENTION

Figure 1:
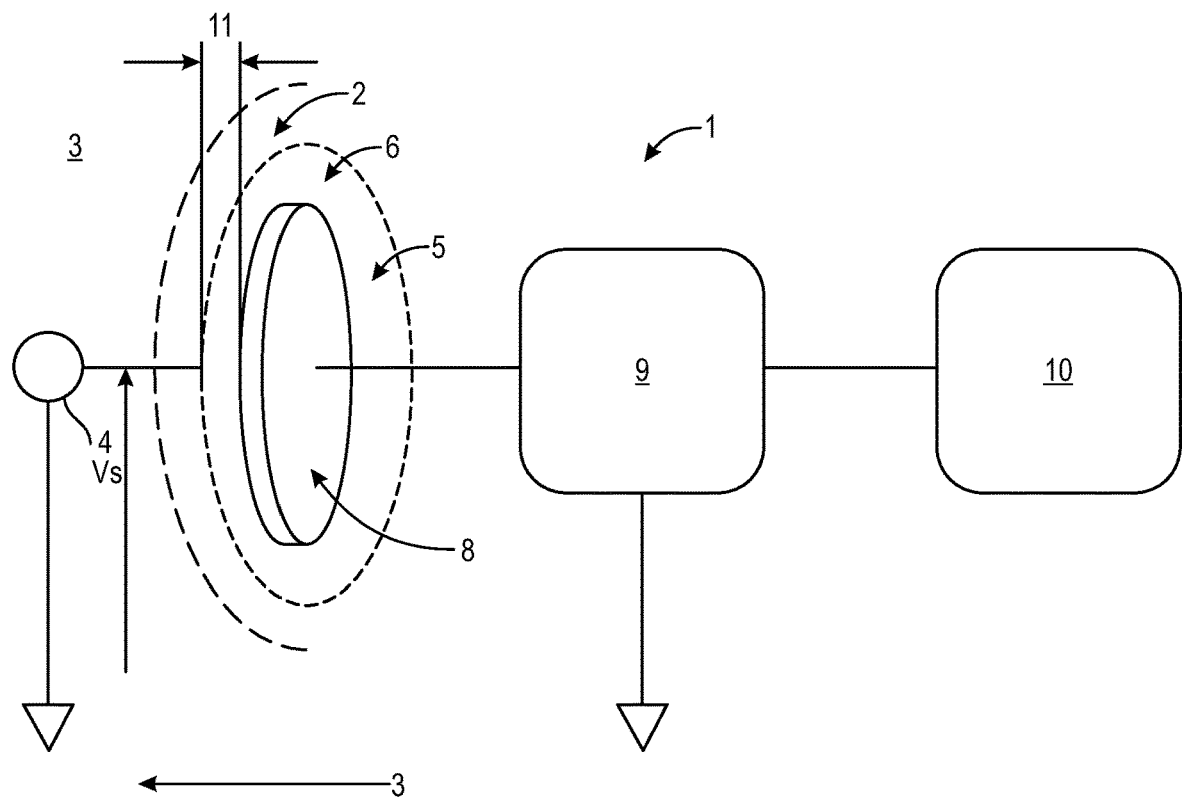
FIG. 1 illustrates a sensing device for biopotential signal according to an embodiment of the invention.
Figure 2:
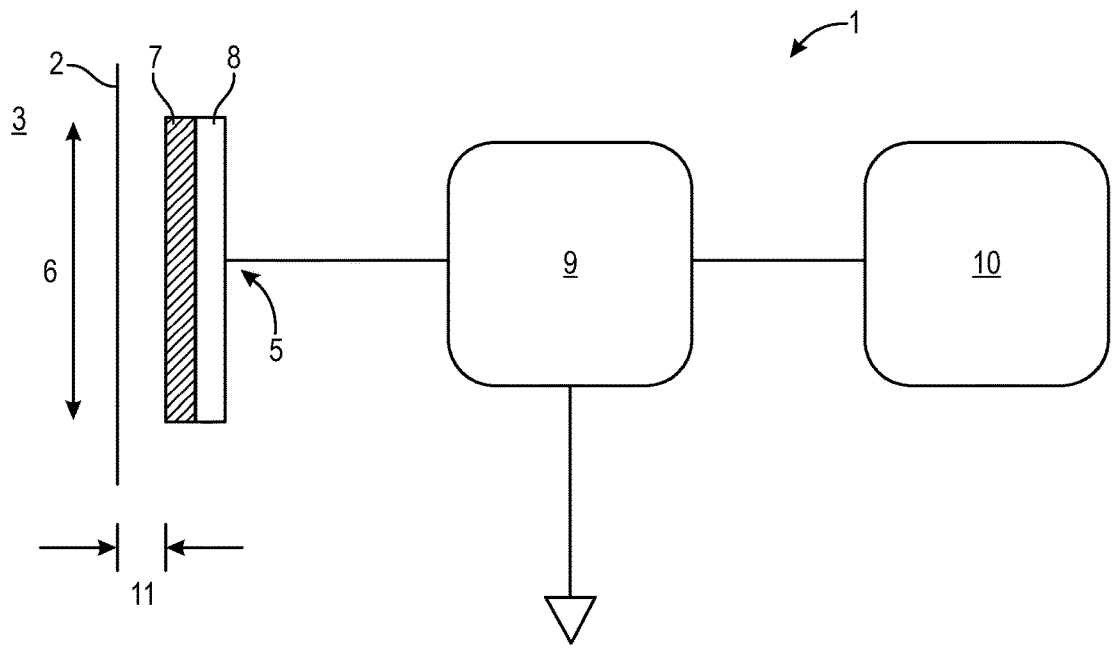
FIG. 2 further illustrates the sensing device of FIG. 1, showing a dielectric layer over the electrode.

FIGS. 1 and 2 illustrate an embodiment of the invention adapted to receive and capture a biopotential signal 1 at a surface 2 of the body 3. The biopotential signal Vs is represented by an ideal voltage source 4.

As illustrated a sensor receiver, or sensor, 5 is located against the surface 2 to receive the biopotential signal 1.

In the scenario illustrated in FIGS. 1 and 2, the sensor receiver 5 is placed against the surface 2. In this example the sensor 5 has dielectric material 7 arranged on the side of an electrode 8 which faces the surface 2 so the dielectric material is arranged between the surface 2 and the electrode 8 and acts as a dielectric.

In this example, the biopotential signal is received over a capacitive connection formed by the surface 2 and electrode 8 which are separated by dielectric layer 7. The dielectric layer acts as a capacitor dielectric. The sensing receiver 5 is connected at a terminal (not shown) to sensing electronics 9. The capacitive connection may be referred to as a signal connection. Impedance parameters of the capacitive connection may be referred to as impedance of the sensor 5, or sensor impedance.

Not shown in FIGS. 1 and 2 are locating means such as adhesive material which locates the sensor 5 at the surface of the body. In this example the body is a biological body and the surface 2 is skin. In this embodiment an adhesive is used to affix the sensor 5 to the skin.

In the example illustrated in FIGS. 1 and 2 the electrode is connected by a terminal 11 to sensing circuitry 9. FIGS. 1 and 2 also illustrate the sensing circuitry 9 connected to a sensing processor 10.

In overview the operation of the sensing device 1 involves the sensor 5 being located at the surface 2 of the body 3 to receive a biopotential signal 4. Sensing circuitry 9 is connected to the sensor 5 and to a signal for a sensing processor 10. The sensing processor determines the biopotential signal from a sensing signal received from the sensing circuitry 9 and dependent on parameter values defining the connection provided by sensor 5 and on parameter values defining operation of the sensing circuitry 9.

An air gap 11 may exist between the sensor 5 and the surface 2. The reader will appreciate that an air gap will represent a low permittivity dielectric for a capacitor formed by the surface 2 and electrode 8. The capacitance will therefore vary with the magnitude of the air gap 11.

An illustration of how the air gap, or distance, between the surface 2 and sensor electrode 8 is given by considering the capacitance C of two opposing electrodes with overlapping area A, separated by distance d over a medium with an effective permittivity ε is given by:

$$C = \varepsilon \frac{A}{d} \qquad \text{Equation 1}$$

where $\varepsilon = \varepsilon_0 \varepsilon_r$, $\varepsilon_0$ is the permittivity of vacuum (8.854 pF/m) and $\varepsilon_r$ is the relative permittivity of the medium between surface 2 and sensor electrode 8 (in this case, air)

Variations in the capacitance of the capacitive connection provided by the sensor 5 will result in variations in the impedance of the connection provided to receive the biopotential signal.

Variations in the impedance of the connection provided by a sensor 5 may be manifest as variations or artefacts on a signal sensed by the device 1.

Variations of the airgap 11 may impact on the capacitive connection provided by the sensor 5. In the case of a real body 3 of a biological subject the magnitude of this air gap 11 will vary.

Variations in the air gap 11, or it's effect, may be over the sensing region 6. Variations in the air gap 11 may be periodic over a time interval in which the biopotential signal 1 is to be sensed, or sampled, and within a frequency range of the biopotential signal. This variation may be an artefact of events in the body. Variation of the air gap 11 may be over an extended time in which sensing may be conducted or in which different sensing samples might be taken. Variations in the airgap may be over time with frequency components outside a frequency range of the bio potential signal, such as a variation which may be caused by the loosening of adhesive, for example, used to locate the sensor 5 on the surface. This variation may be as a DC drift in capacitance and/or in the biopotential signal as sensed by the device 1. Other variations may be at frequencies above the frequency range of a biopotential signal such as might be caused by high frequency vibration. Variations in the air gap may be any combination of the variations discussed above.

In similar scenarios to that illustrated in FIGS. 1 and 2, other effects may impact on the impedance of the connection provided by the sensor receiver. For example, effects at the skin of a subject may affect the permittivity of the dielectric properties of the capacitor formed by the surface 2 and electrode 8.

Figure 3:
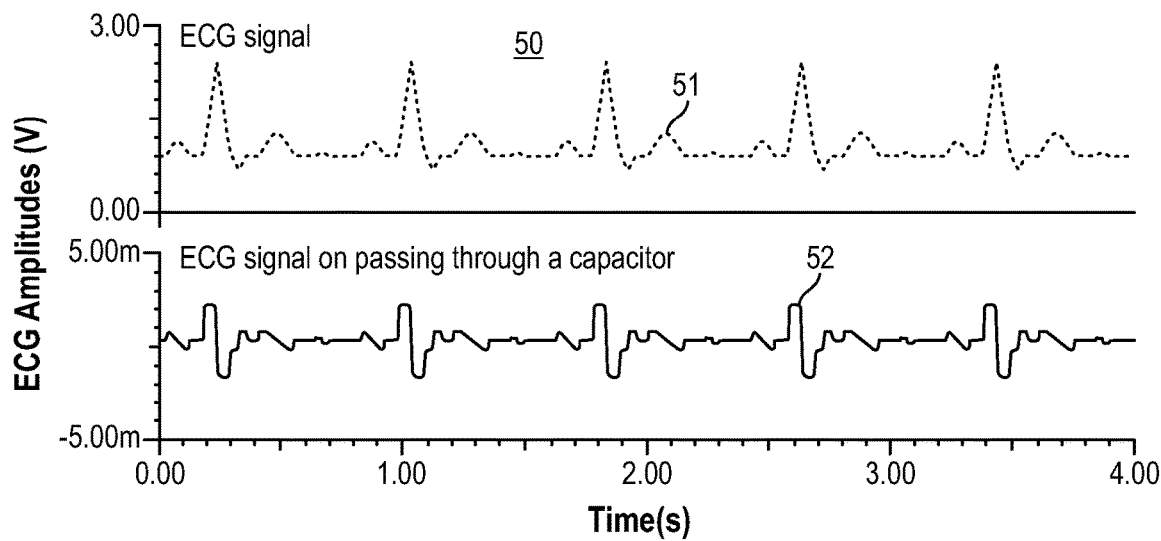
FIG. 3 illustrates a biopotential signal which various embodiments of the invention are adapted to sense.

An example effect of variations in the capacitance on a biopotential signal are illustrated in FIG. 3. In this example the biopotential signal is an Electrocardiography signal (ECG).

The upper trace 51, as shown, illustrates an example simulated ECG signal. The lower trace 52 illustrates the ECG signal $V_{ecg}$ (equivalent to Vs of FIGS. 1 and 2) sensed as a displacement current id after the effect of a capacitance C.

$$i_d = C \frac{dV_{ecg}}{dt} \qquad \text{Equation 2}$$

The reader may recognise the effect of the capacitance C is to differentiate $V_{ecg}$.

As described above, air acts as a dielectric for a capacitor formed by the surface 2 and sensor 3 with a low dielectric constant $\varepsilon_r=1$. As the air gap of the sensor from the surface increases, the air gap capacitance $C_{air}$ decreases and the low frequency ECG signal gets differentiated and attenuated.

The applicant has observed that mitigating the effect of an air gap will allow sensing of an ECG, for example, more robust over variations in an air gap between the surface and the sensor receiver. This may allow sensing of ECGs from a distance away from the surface 2 of the body 3 of a subject or may allow variations caused by phenomena occurring at a body to be mitigated.

Figure 4:
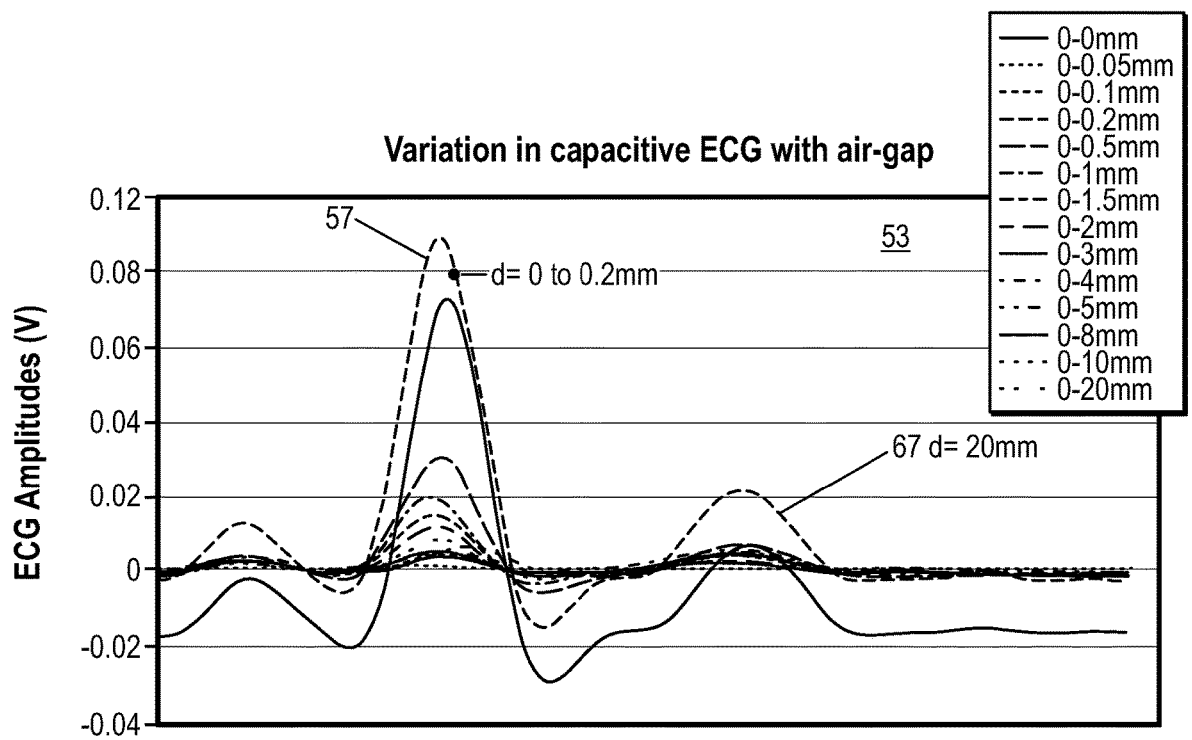
FIG. 4 illustrates the effect of an air gap between an electrode of the sensing device of FIG. 1.

FIG. 4 shows a plot 53 with traces 54 to 67 for different air gaps illustrating the effect of air gap on an ECG signal of voltage 1V sensed capacitively by another embodiment of the invention, where d represents the change in distance (in mm). A very slight change in ECG amplitudes is observed at air gaps=0.2 mm with trace 54. The designed sensor is capable of sensing ECG signals in real conditions from a distance of up to 20 mm, without the incorporation of circuit improvisation techniques such as guarding and shielding.

Configurations of various embodiments of the invention which further mitigate the effect the 'air gap effect' are discussed below.

Figure 5:
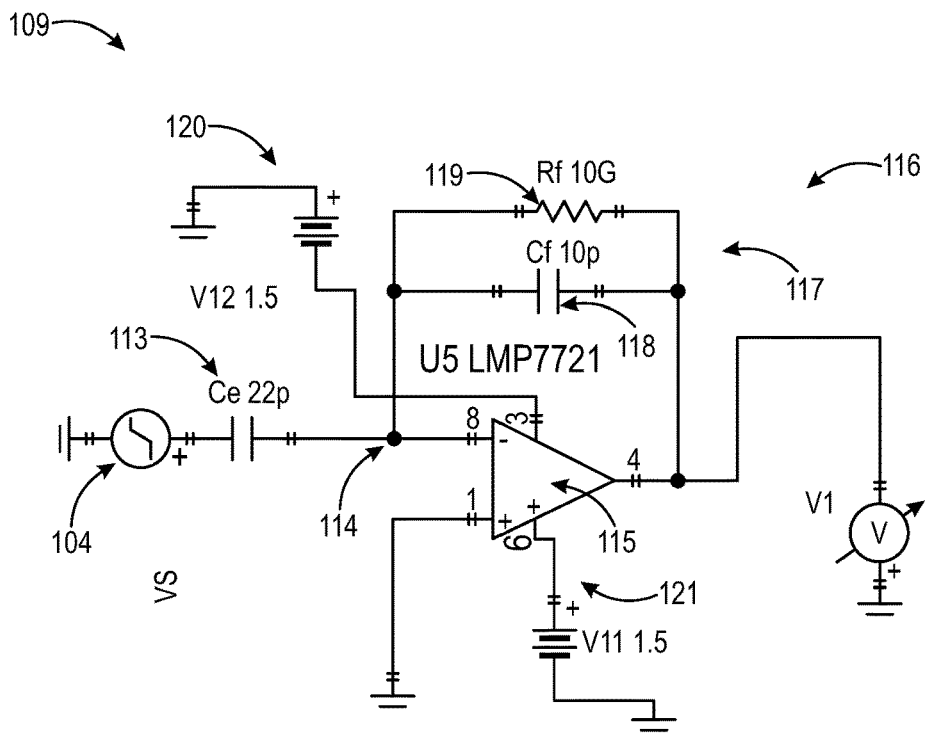
FIG. 5 illustrates circuitry representing a biopotential signal, sensor element and sensing circuitry of the embodiment of FIG. 1 and FIG. 2.

FIG. 5 illustrates circuitry representing a sensor (not shown) and sensing circuitry 109 according to another embodiment of the invention. In this illustration the capacitance Ce represents an unknown capacitance of a signal connection a series capacitance 113 connected between the ideal voltage source 104 and the inverting input 114 of an operational amplifier 115. This capacitance 113 is made up of the capacitance between the body (not shown, but similar to 3 in FIG. 1) and a sensing electrode (not shown but similar to 8 in FIG. 1) and also by a series capacitance connected at the input 114 of the Op-Amp 115 as a series capacitance of a charge amplifier circuit 116. In practice specific implementations of this embodiment may have series capacitances connected to the sensor receiver (not shown) to set the capacitance Ce 113 at an optimal value. However, this may be problematic because the capacitance formed by the body (not shown) and the sensor receiver (not shown) is not known, is not precisely known or varies with effects occurring at the body or skin of the body or because of a combination of these. Similarly, and impedance associated with the capacitance will be unknown.

The charge amplifier circuit 116 is formed of an operational amplifier 115 with supply voltages, feedback components 117 and series components forming part of the capacitance 113. As the reader will appreciate the feedback and series components provide feedback and series impedances with known parameter or component values which determine a transfer function for the charge amplifier according to Kirchhoff's laws applied at the node 114 of the Op-Amp with assumptions for the operational amplifier well known to the reader. In this specific example the feedback impedance is provided by a feedback resistance $R_f$ 119 and a feedback capacitance $C_f$ 118, in parallel. The gain of the charge amplifier 115 will be determined by the feedback impedance and the series capacitance 113, which includes both the sensor capacitance and any series capacitance included in the charge amplifier circuit 116.

The reader may recognise the sensor connected to the circuit 116 as a signal channel where the circuit has a transfer function defined by known components and where the transfer function of the channel is dependent on the known component values and also on an unknown impedance parameter of the signal connection provided by the sensor. For example, the capacitance of the signal connection may vary by an unknown value may vary over an unknown range of values.

The sensor circuitry of the embodiment of FIG. 5 provides gain determined, or selected, dependent on an expected noise floor for the biopotential signal. In this example the expected noise floor is determined by background electromagnetic emissions.

The components of the embodiment illustrated in FIG. 5 are also determined, on the following considerations. One consideration is that the corner frequencies of the charge amplifier are outside a range of frequencies of the biopotential signal. Another consideration is that the lower corner frequency eliminates DC drift which may occur due to effects of the body (not shown), occurring at the surface of the body at a sensing region (not shown) defined by the sensor (not shown). In the example shown the lower corner frequency is determined to mitigate the effects of the air gap which occurs between the body (not shown) and the sensor (not shown). In the example shown the lower corner frequency is determined to mitigate artefacts of breathing of the subject which affect the air gap between the body (not shown) and the sensor (not shown).

Table 1, below, lists values for the capacitance Ce 113, providing a series impedance, of charge amplifier and noise levels of biopotential signals captured via a resistive connection to the body (not shown) and a capacitive connection to the body (not shown).

TABLE 1

Values of series capacitance of charge amplifier used for sensor circuitry.

| Value of series capacitance (pF) | Noise level (peak to peak) for resistive sensing | Noise level (peak to peak) for capacitive sensing |
| --- | --- | --- |
| 22 | 0.056 | 0.05 |
| 470 | 0.9 | 0.8 |
| 2200 | 2.5 | 1.8 |

Figure 6:
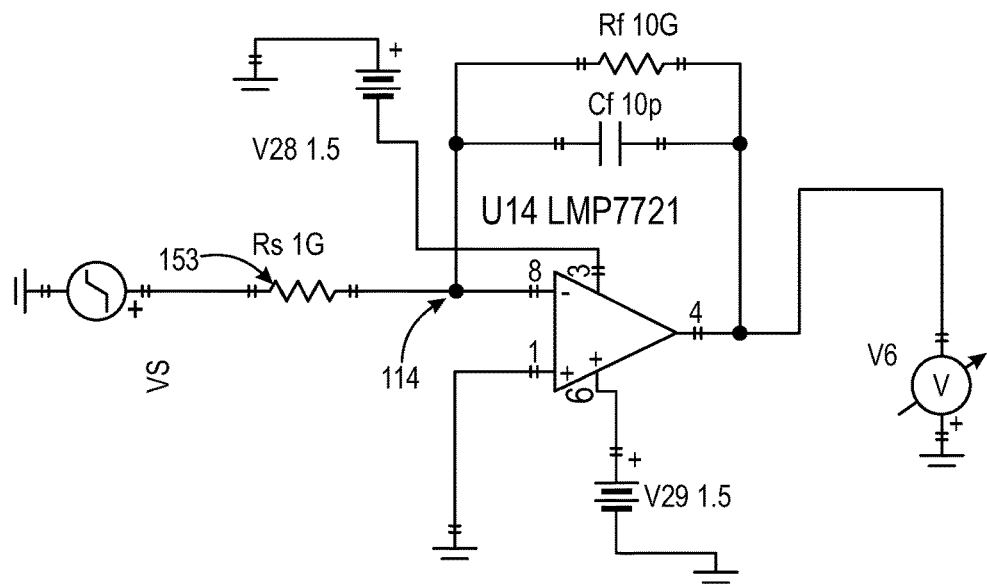
FIG. 6 illustrates circuitry representing a biopotential signal, sensor receiver and sensing circuitry of an alternative embodiment of FIG. 5.

FIG. 6 illustrates a charge amplifier with a resistive sensor according to an alternative embodiment of the invention to FIG. 5. In this example the resistive sensing arrangement according to various embodiments involves a direct conductive connection to a surface of a body and this connection is characterised by a resistance 153.

An Op-Amp, LMP7721MA, is used in the sensing circuitry 109 of the embodiment illustrated with reference to FIG. 5. The selection of this Op-Amp is due to ultra-low input bias current characteristics of the LMP7721MA.

Figure 7:
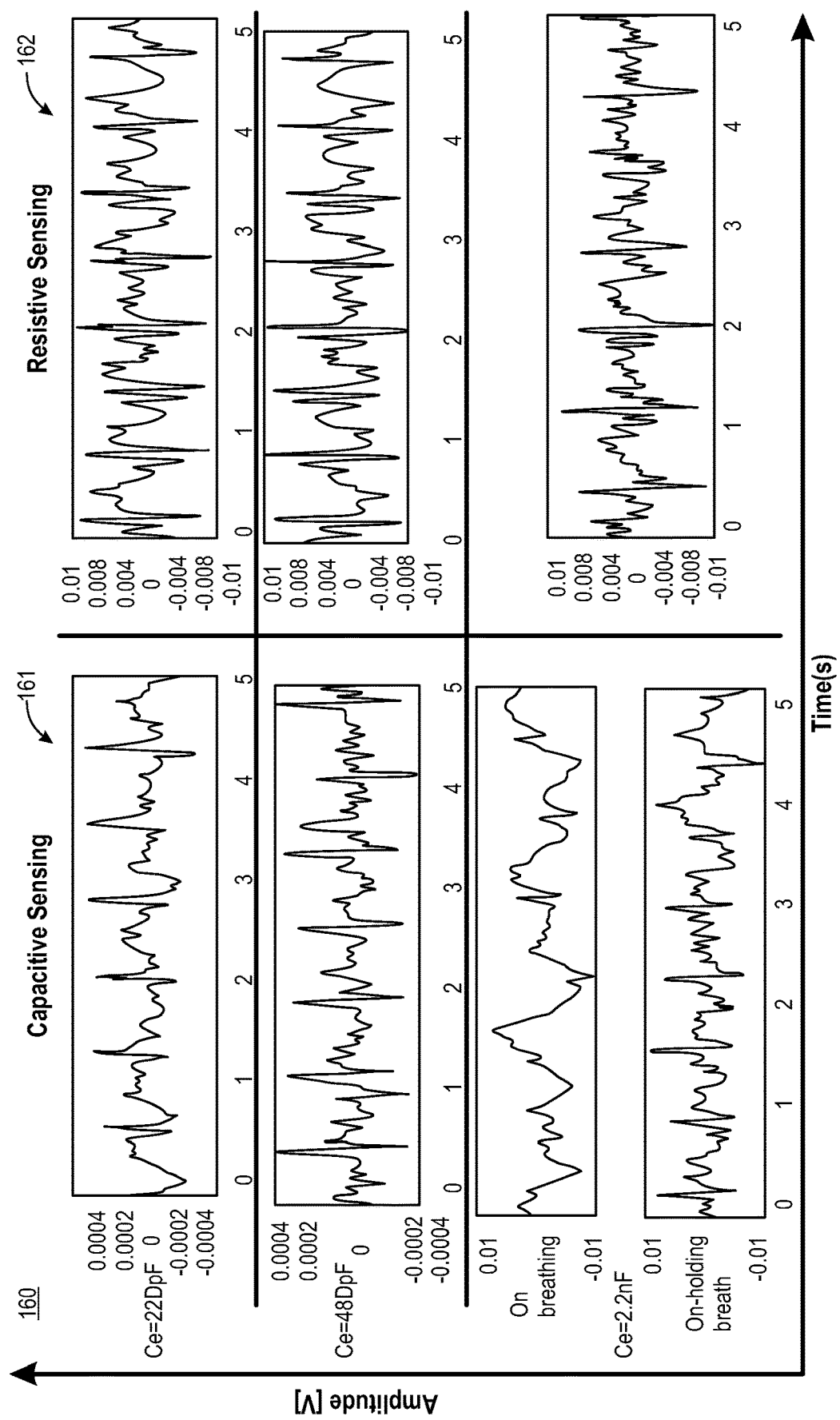
FIG. 7 illustrates biopotential signals to be sensed and after sensing by sensor and sensing circuitry of the embodiments of FIG. 5 and FIG. 6.

FIG. 7 shows plots 160 illustrating the effect on noise of the various capacitance values listed in Table 1 with traces 161 of biopotential signals sensed with capacitive sensing arrangement of embodiments of the invention illustrated with reference to FIGS. 1 and 2 traces 162 for traces of biopotential signals sensed with a conductive sensing arrangement of alternative embodiments.

Table 2 lists component values used for a charge amplifier of the embodiments of the invention illustrated with reference to FIG. 5 and FIG. 6.

TABLE 2

Values of components for sensing circuitry.

| Passive Circuit Component | Desired Value/range |
| --- | --- |
| Rf | 10 G ohm |
| Cf | 10 to 100 pF |
| Cs | 22 to 500 pF |
| Rs | 100 Meg to 1 G |

The charge amplifier circuitry of FIGS. 5 and 6 with component values listed in Table 2 are selected to be within the following regime corresponding to the principles discussed above.

The charge amplifier 116 restores the ECG wave shape of a signal received at a sensor at a surface of a body by integrating the signal differentiated due to air gap or series capacitance between the surface of the body and the electrode of the sensor.

Integration is only possible if $$(r_f \times C_f) > (R_s \times C_f) \quad \quad 3$$

where $R_f$ and $C_f$ are the feedback values of resistance and capacitance and is $R_s$ the series resistance.

A series capacitor forming part of 113 Cs and the charge amplifier circuit 116 provides differentiation of the signals prior to their integration, wherein the corner frequencies of the charge amplifier are within the ECG frequency range.

Corner frequencies of the charge amplifier circuit are:

$$f_a = \frac{1}{2\pi R_f C_f}, \text{ and,} \quad \quad \text{Equation 4}$$

$$f_b = \frac{1}{2\pi R_s C_f} \quad \quad \text{Equation 5}$$

In cases where there is no series capacitance 113 in the circuit, there is only one corner frequency (lower cut off $f_a$).

Anticipated ECG frequency range is between 0.5 Hz to 150 Hz. ECG components lying within the range of the corner frequencies will be integrated.

Selections of the values of $R_f$, $C_f$, Ce' and $R_s$, are made for the charge amplifier, such as 116, where Ce' is the capacitance between the surface of the body and the electrode 106 of the sensor 105, making up part of Ce 113 which includes the capacitance formed by the sensor.

The reader will appreciate that the charge amplifier 114 follows an inverting amplifier configuration, for which the gain can be expressed as follows.

$$G = -\frac{Z_f}{Z_s} \quad \quad \text{Equation 6}$$

where $Z_f$ is the feedback impedance and $Z_s$ is the series impedance, provided by Ce' for example.

The sensing circuitry 109 operates in a regime defined by selections of feedback components and series components of charge amplifier, with feedback and series components providing feedback and series impedances where the gain determined Equation 6 is great enough to amplify the biopotential signal above a noise floor and where the feedback components including a capacitor in parallel with a resistor defining a corner frequency defined by Equation 4 above the biopotential signal frequency range to not filter out components of the biopotential signal and where the series components are selected to provide a corner frequency defined by Equation 5 far enough below the biopotential signal to not filter the lower frequency components of the biopotential signal and selected to also have an impedance which is greater than the anticipated impedance of the connection for the biopotential signal provided by the sensor receiver. The biopotential signal used in this for these selections is a biopotential signal which is anticipated as being sensed. Similarly, in this example noise floor may be an anticipated noise floor.

The reader will recognise equivalent regimes with non-inverting amplifiers or with other equivalent circuitry of alternative embodiments.

Figure 8:
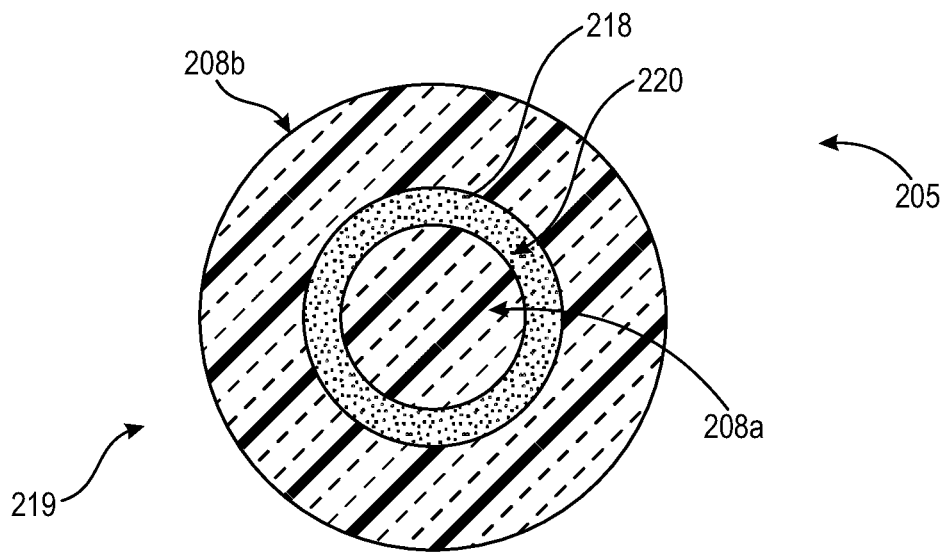
FIG. 8 illustrates a sensor according to further embodiment of the invention.

FIG. 8 illustrates a sensor, or sensor receiver, 205 according to another embodiment of the invention. The sensor receiver 205 has first and second sensor electrodes 208a and 208b which are able to form first and second signal connections with a body (not shown). Each electrode is able to receive the biopotential signal and connect it to the terminal with an impedance which differs between the first and second receivers. The first and second electrodes each lie within a sensing periphery 219 which defines a sensing region for the biopotential signal. Each electrode 208 is assumed to receive the same biopotential signal in the sensing region via a distinct signal connection formed with the body by each electrode. Alternatively, the sensing region is dimensioned to the highest spatial resolution at the surface of the body required for sensing of a biopotential signal.

As shown in FIG. 8, 208a is a conductive area forming one plate of a capacitor and 208b is a conductive area electrically isolated from 208a. The reader will appreciate that a conductive area, such as 208a for example, will form capacitances with both the body and the other capacitive area 208b, for example.

The electrodes 208a and 208b each provide an impedance for the biopotential signal. In the example of FIG. 8 the sensor is capacitive, and the impedance is capacitive as known to the reader. The sensor 205 is arranged so that the electrodes each have an impedance with a defined approximate relationship with each other. For example, a second electrode 208b may provide a second signal connection which has an impedance which is defined by a known relation to the impedance of a first signal connection provided by the first electrode 208a. The relationship may be that the second electrode 208b is a factor of the impedance of the impedance provided by the first electrode 208a. In the specific example shown the factor is two.

The reader will appreciate that the electrodes do not likely provide purely capacitive connections defined by a scalar separation of the electrode from an electrode representing the skin.

Therefore, there may be known and unknown impedance parameters if the signal connection. In these cases the electrodes 208b will be arranged to provide a second signal connection which has an unknown impedance parameter which is defined by a known relation to an unknown impedance parameter of a first signal connection provided by the first electrode.

In this example the impedance is provided by a capacitance and the relationship between the electrodes 208a and 208b is provided substantially by the electrode 208a having an area that is larger by a known factor. The electrodes 208a and 208b are aligned in the same plane and separated spatially by an insulator 220. In this case the insulator is an annular sheet of dielectric material. In this case an unknown first impedance parameter of the first signal connection may be a capacitance formed between the first electrode 208a and a body. Alternatively, an unknown first impedance parameter may be a reactance of the first signal connection provided by the first electrode 208a.

Figure 9:
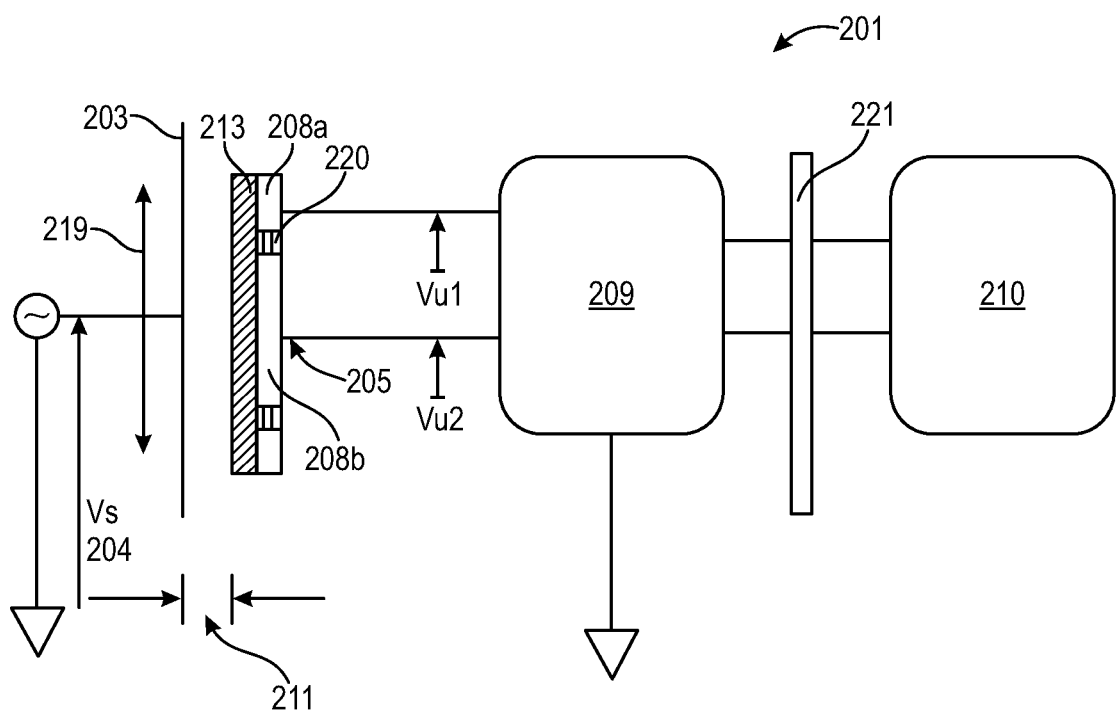
FIG. 9 illustrates a biopotential signal element, sensing circuitry and sensing processor according to embodiment of the invention of FIG. 8.

FIG. 9 illustrates a sensor device 201 made of a sensor 205, sensing circuitry 209, a sensing processor 210 able to perform data operations and connected to the sensor circuitry by a data bus 221. The sensor circuit receives first and second electrode signals from the first and second electrodes 208a and 208b and outputs first and second sensor signals to the bus 221 as channels of a data signal.

The sensor device 201 has the sensor receiver of FIG. 8 with each electrode 208a and 208b connected to sensing circuitry 209.

A layer of dielectric material 213 is located between the electrodes 208 and a surface 202 of a body 203. An air gap 211 is shown between the sensor receiver 205 and the surface 202 to illustrate a gap that may occur inadvertently.

The first and second electrode signals received by the sensing circuitry 209 are unknown voltages Vu1 and Vu2 which are caused by the same biopotential signal with first and second sensor impedances. First and second sensor impedances are formed by different ones of the first electrode and second electrode, respectively, with the surface of the body.

As discussed above, the specific example of FIGS. 8 and 9 the connection for the biopotential signal is formed by a capacitance between the surface 202 and the electrode 208a or 208b. In the example of FIGS. 8 and 9 the area of the electrode 208a has an area which forms a first sensor capacitance with the surface 202 that has a defined relationship with a second sensor capacitance 208b. An unknown second capacitance, or other impedance parameter, may be considered dependent on the unknown first capacitance by the known relationship. In the specific example of this embodiment the defined relationship is that the capacitance formed by the second electrode 208b is a factor of the capacitance formed by the first electrode 208a. In this specific example the factor is two. In the example illustrated with reference to FIGS. 8 and 9 the relationship between the first and second sensor capacitances, or other unknown impedance parameters associated with these capacitances, is determined substantially by the relative areas of the first electrode 208a and the second electrode 208b. In this example, the sensor receiver 205 is arranged to provide a similar air gap with the surface 202 and each of the electrodes 208a and 208b and the sensor receiver has a similar dielectric material and similar thicknesses of dielectric material between the first electrode and the surface and between the second electrode and the surface. Therefore, in this example electrodes having areas in which one is a factor of the other will provide capacitances which are approximately the same factor of each other by Equation 1.

The series impedance $Z_{a1}$ between an ideal voltage signal representing a biopotential signal and sensing circuitry 209 will be related similarly to the relationship of capacitances formed between electrodes 208 and the surface 202. The impedance between the biopotential signal and each input 221a and 221b of the sensing circuitry 209 will differ by approximately the same factor as the area of the capacitances by the following equation for $Z_a$, considered as a capacitive impedance defined by the dimension of the electrode on the sensor.

$$Z_a = \frac{1}{sC_a} \qquad \text{Equation 7}$$

where $C_a$ depends on the electrode size, $$C_a = \varepsilon_0 \varepsilon_r \frac{A}{d} \qquad \text{Equation 8}$$

$\varepsilon_0$ is the permittivity of free space, $8.85 \ast 10^{-12}$ F/m, $\varepsilon_r$ is the relative permittivity of the medium, A is the area of the electrode and d is the thickness of the medium or distance between electrodes forming the capacitance, such as the surface 202 and an electrode 208a.

As apparent from Equation 7 the dimension and/or area, A of the second electrode 208b as a multiple of the area of the first electrode 208a achieves a capacitance of n $C_a$, where n is the ratio of the area of the two electrodes and Ca is the capacitance formed by the surface 202 and the first electrode 208a.

By Equation 4, substantially a similar multiple of impedances seen by a signal via the second electrode 208b versus the first electrode 208a can be arranged.

The processor of the embodiment of FIG. 9 receives a signal from each of two channels of the sensing circuitry where each channel applies a respective defined transfer function to the signals received at the electrodes 208a and 208b.

The embodiment illustrated with reference to FIGS. 8 and 9 determines the biopotential signal independently of sensor impedances formed between the surface 202 and the each of the electrodes 208a and 208b sensors. The sensor signal is determined by signals at multiple output channels of the sensing circuitry 209, transfer functions for the output channels of the sensing circuitry 209 and a defined relationship between the sensor impedances and the defined relationship of the first electrode 208a and second electrode 208b.

Figure 10:
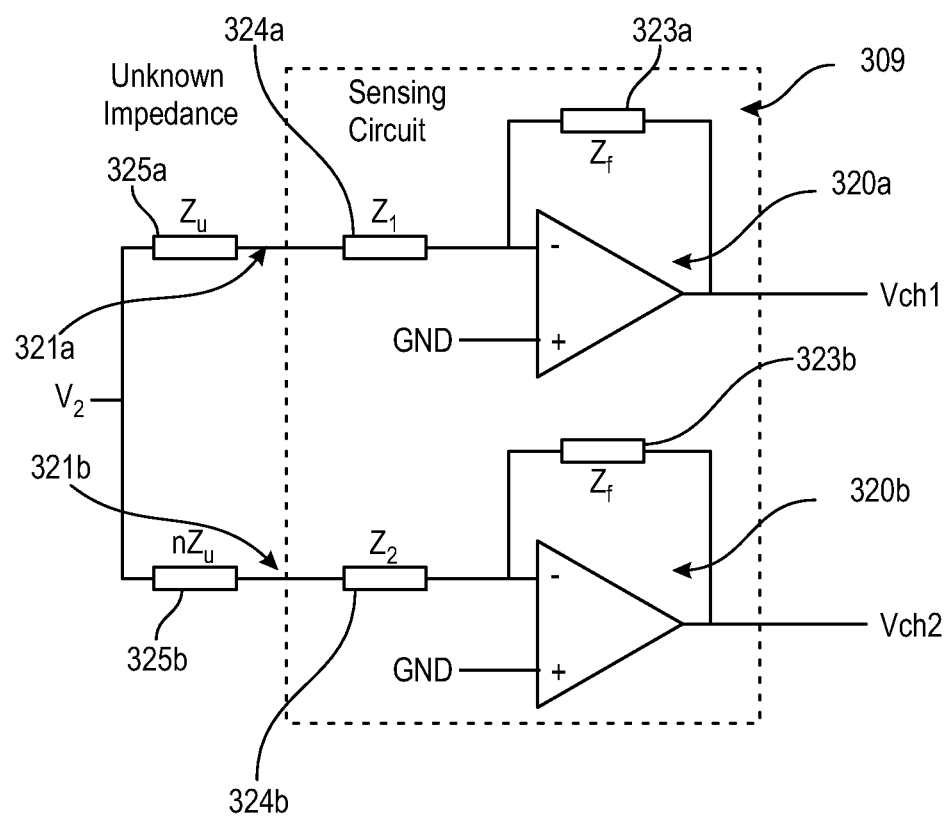
FIG. 10 illustrates circuitry representing a biopotential signal, sensor receiver and sensor circuitry of a further embodiment of the invention similar to that of FIG. 8 and FIG. 9 with specific implementation of sensor receiver and sense of circuitry.

Determining a biopotential signal independently of the impedance according to the invention is illustrated with reference to FIG. 10 showing sensing circuitry 309 according to a further embodiment of the invention. The sensing circuitry 309 may be connected to a sensor 205 as illustrated in FIG. 8 with an electrode 208a providing a connection with impedance $Z_{u1}$ 325a and with an electrode 208b providing a connection with impedance $H_{12}Z_{u1}$ 325b.

The sensing circuitry 309 has two charge amplifiers 320a and 320b formed of inverting operational amplifier circuits which each provide a transfer function between inputs 321a and 321b and outputs 322a and 322b. The transfer function is defined by feedback impedances $Z_{f1}$ 323a and $Z_{f2}$ 323b and series impedances $Z_{s1}$ 324a and $Z_{s2}$ 324b.

The impedances 325a $Z_{u1}$ shown in FIG. 10 represents an unknown impedance of a signal connection formed between the surface of a body (not shown) and a first electrode (not shown) of a sensor receiver (not shown). The impedance 325b $H_{12}Z_{u1}$ shown in FIG. 10 represents the unknown impedance between the surface of a body and a first electrode (not shown) of a sensor (not shown). In this example the sensor receiver is arranged so that the impedance 325b is a factor $H_{12}$ of the impedance 325a. In this example also, the series impedances are illustrated as separate to impedances 325a and 325b formed by the electrode-surface interfaces.

The invention will now be illustrated for example embodiments using two channels, both channels using inverting amplifiers as receiver circuits, using different unknown impedances related by H12 to represent a signal connection formed by the sensor device where the impedance may be unknown or variable, and with the processor reading only voltage.

Mitigation, cancellation or nullification of effects involving $Z_{u1}$ or capacitance, due to an air gap at a sensor-body interface (not shown) according to the embodiment of the invention of FIG. 10 is illustrated below.

The equations for the two channel outputs 322a and 322b, following the above circuit, can be defined as:

$$V_1 = -\frac{Z_{f1}}{Z_{s1} + Z_{u1}} V_{in}, \text{ and,} \qquad \text{Equation 9}$$

$$V_2 = -\frac{Z_{f2}}{Z_{s2} + H_{12}Z_{u1}} V_{in} \qquad \text{Equation 10}$$

where $V_{in}$, $V_1$, $V_2$, are in the frequency domain.

The value of $Z_{u1}$ is unknown and changes with time, however the value of $H_{12}$ is known. From equations 9 and 10:

$$(V_1 \times Z_{s1}) + (V_1 \times Z_{u1}) = -Z_{f1} \times V_{in},$$

$$(V_2 \times H_{12} Z_{u1}) = -Z_{f2} \times V_{in}, \qquad 11$$

Eliminating the value of $Z_{u1}$ and solving equation 11:

$$V_{in} = \frac{V_1 V_2 (H_{12} Z_{s1} - Z_{s2})}{-H_{12} V_2 Z_{f1} + V_1 Z_{f2}} \qquad \text{Equation 12}$$

Equation 13 deliberately omitted.

Using Equation 9 input signal $V_{in}$ can be reconstructed from known parameters $V_1$, $V_2$, $H_{12}$, $Z_{s1}$, $Z_{s2}$, $Z_{f1}$ and $Z_{f2}$.

As the transfer function of the sensing circuitry 309 is in the Frequency domain, $V_{in}$ can be determined by the following steps:

a. Acquiring $V_1$ and $V_2$ sampled at a frequency Fs (above 250 Hz for an ECG signal)
b. Taking a discrete Fourier transform (FFT) of $V_1$ and $V_2$.

$$FFT(V_1) = \hat{V}_1(k) = \sum_{j=0}^{N-1} V_1(j) e^{-2\pi i k j/N} \qquad \text{Equation 14}$$

$$FFT(V_2) = \hat{V}_2(k) = \sum_{j=0}^{N-1} V_2(j) e^{-2\pi i k j/N} \qquad \text{Equation 15}$$

Where N is number of samples in $V_1$ and $V_2$ and k=0 to N−1, i=sqrt(−1).

c. From Equation 12, $$\hat{V}_{recon} = \frac{\hat{V}_1 \hat{V}_2 (H_{12} Z_{s1} - Z_{s2})}{-H_{12} \hat{V}_2 Z_{f1} + \hat{V}_1 Z_{f2}} \qquad \text{Equation 16}$$

where $\hat{V}_{recon}$ is the reconstructed ECG in frequency domain.

From Equation 16 it can be inferred that the denominator becomes 0 if $$\frac{\hat{V}_1}{\hat{V}_2} = H_{12} \text{ and } Z_{f1} = Z_{f2}, \text{ and,} \qquad \text{Equation 17}$$

The numerator becomes 0 if $$\frac{Z_{s2}}{Z_{s1}} = H_{12} \qquad \text{Equation 18}$$

Therefore, for reconstruction, the following conditions need to be satisfied:

$$\frac{\hat{V}_1}{\hat{V}_2} \neq H_{12} \text{ and } \frac{Z_{s2}}{Z_{s1}} \neq H_{12} \qquad \text{Equation 19}$$

Taking the inverse Fourier Transform (IFFT) to transform the reconstructed signal from frequency domain to time domain.

$$V_{recon} = IFFT(\hat{V}_{recon})$$

$$IFFT(\hat{V}_{recon}) = V_{recon}(j) = \frac{1}{N} \sum_{k=0}^{N-1} \hat{V}_{recon}(k) e^{-2\pi i k j/N} \qquad \text{Equation 21}$$

where j=0 to N−1 Adaptions to Equations 9 to 21 for a similar circuitry with each channel having different $Z_f$ values will be apparent to the reader.

Adaptions to Equations 9 to 21 for circuits equivalent and alternative to an inverting amplifier will also be apparent to the reader.

A process (S1) for determining the biopotential signal carried out by a processor 310 of the embodiment of the invention illustrated with reference to FIG. 11 using the approach illustrated in FIG. 11.

The process takes the two channels—$V_1$ and $V_2$ output by sensing circuitry 309 and computes the input voltage $V_{in}$ for a biopotential signal through the above equations.

At Step S1-1 of the process, signals at each channel of the sensing circuitry are acquired. In this example $V_1$ and $V_2$ are sampled by the processor 310 at a sampling frequency Fs. In this example the acquired signals are stored in a volatile memory of the processor.

At S1-2 the acquired signals are 'windowed', as will be understood by the reader, to a multiple of the sampling frequency Fs. For example:

$$V_1 = V_1(Fs:5*Fs) \qquad 22$$

At S1-3 fast Fourier transforms of the sampled signals are computed and stored to provide signals in the frequency domain. For example, $$\hat{V}_1 = FFT(V_1) \qquad 23$$

$$\hat{V}_2 = FFT(V_2) \qquad 24$$

At S1-4 point-by-point multiplication of $\hat{V}_1$ and $\hat{V}_2$ is performed to calculate $\hat{I}$, where:

$$\hat{I} = \frac{\hat{V}_1 \times \hat{V}_2}{H_{12} \hat{V}_2 - \hat{V}_1} \qquad \text{Equation 25}$$

At S1-5 the Transfer Function of the sensing circuitry is computed.

In one example, corresponding to the sensing circuitry illustrated with reference to FIG. 10, a processor operation equivalent using equation 23 is performed using known values of parameters $Z_s1$, $Z_s2$, $Z_f$ and $H_{12}$. The following parameter values are used in this example: $Z_s1$ and $Z_s2$, the series impedances in the channel circuit, comprised of either a capacitance per channel $C_{e1}$ and $C_{e2}$ or a resistance with a capacitance in each channel ($R_{s1}+C_{e1}$, $R_{s2}+C_{e2}$), $H_{12}=2$ (based on the ratio of area of electrodes which was 2). The range of $R_{s1}$ and $R_{s2}$ is between 0 to 100 MOhms. $C_{e1}$ and $C_{e2}$ were chosen such that $C_{e2}/C_{e1}$ is not equal to $H_{12}$. The range of values is between 22 pF to 500 pF. $Z_f$, the feedback impedance comprises of resistance $R_{fin}$ parallel with a capacitance $C_f$.

The total feedback impedance is:

$$Z_f = \frac{R_f}{1 + sR_f C_f} \quad \text{Equation 26}$$

The values of $R_f$ and $C_f$ were chosen to be 10-50 GOhms and 100-10 pF.

At S1-6 the frequency response of transfer function TF(s) is computed as a set of values at each frequency 2.

At S1-7 the reconstructed biopotential signal $\hat{V}_{recon}$ is determined in the frequency domain by operations equivalent to:

$$\hat{V}_{recon} = TF \times \hat{I} \quad 27$$

At S1-8 the biopotential signal is determined it time domain from the frequency domain an inverse fast Fourier transform:

$$V_{in}(t) = \text{IFFT}(\hat{V}_{recon}) \quad 28$$

The invention will now be illustrated for embodiments with generalised receiver circuits and electrodes.

Various embodiments of the invention may use alternative sensing circuitry to the charge amplifier operational amplifier circuitry illustrated. The invention using generalised sensing circuitry is illustrated with reference to FIG. 12 by the treatment below.

Figure 12:
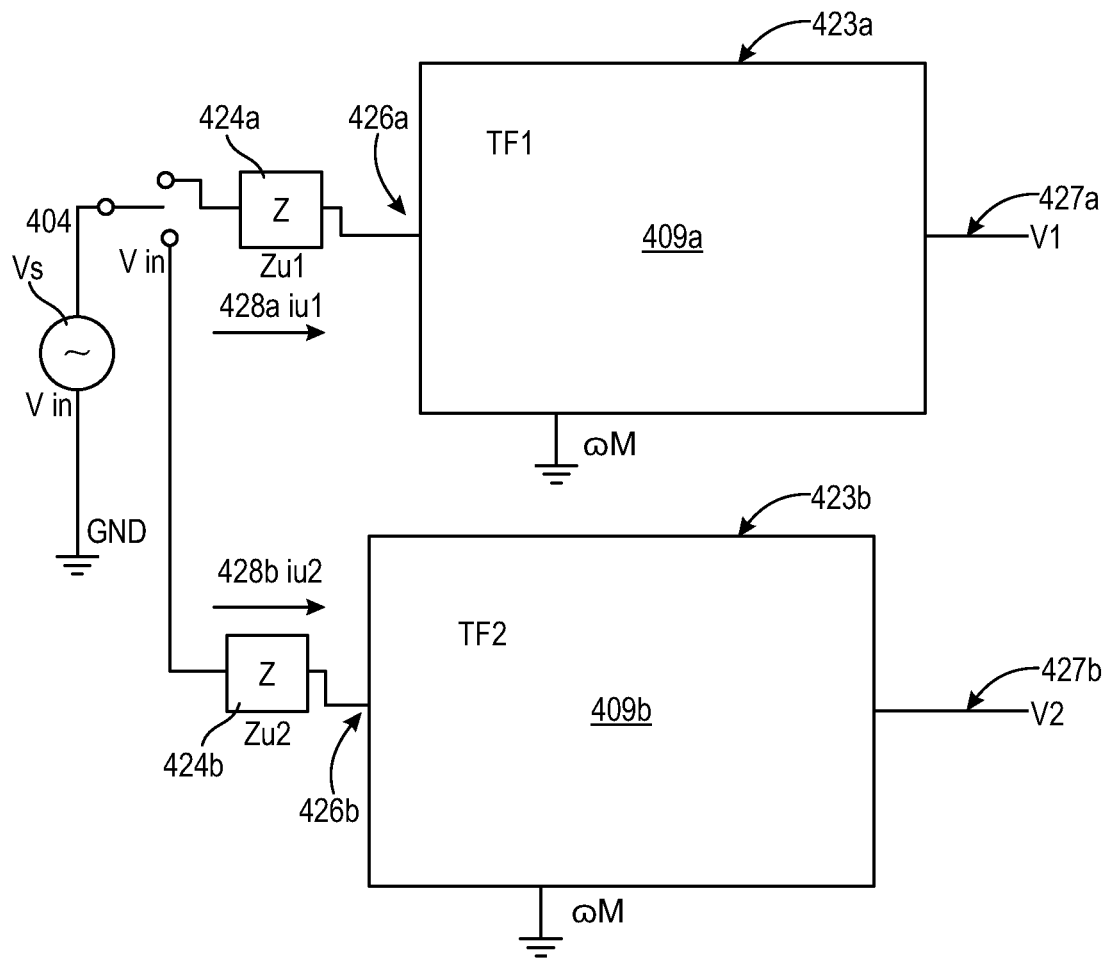
FIG. 12 illustrates circuitry representing a biopotential signal, sensor receiver and generalised sensing circuitry according to various additional embodiments of the invention.

FIG. 12 illustrates sensing circuitry 409 for sensing a biopotential signal sourced by first and second sensing channels (423a and 423b) which form connections with the surface of a body (not shown) in a sensing region (not shown).

FIG. 12 illustrates an ideal voltage 404 Vin, representing a biopotential signal. Impedances 425a and 425b represent first and second sensor impedances of first and second sensing channels formed with the surface of the body (not shown) to receive the biopotential signal.

The sensing channels are arranged as illustrated herein so that the first and second sensor impedances 425a and 425b have substantially a defined relationship $$Z_{u1} = Z_u, Z_{u2} = H_{12} Z_{u1} + k_{12} \quad 29$$

The sensing circuitry 409a and 409b provide sensing signals at first and second outputs 427a and 427b. The sensing signals are provided dependent on first and second sensing channel signals received by the circuitry 409 at first and second sensing terminals 426a and 426b.

Consider the sensing circuitry of FIG. 12 representing a general form of the proposed measurement system.

The impedances 425a $Z_{u1}$ and 425b $Z_{u2}$ are unknown and/or variable. In the example of the electrodes (not shown) forming a capacitive connection with the surface of the body (not shown), the impedances $Z_u$ may change due to changes in an air gap between the electrodes and the surface of the body. Also in the example of the electrodes (not shown) forming a capacitive connection, changes of permittivity of any dielectric materials between the electrodes and the body may change the impedances $Z_u$.

The sensing circuitry 409 provides a sensing signals at outputs 427a and 427b after a defined transfer function is applied.

The invention will now be illustrated for example embodiments using two-channels, op-amp circuit for the receiver circuits, different impedances for the signal connections provided by the sensor electrodes, and the processor measuring voltage and current.

The transfer function may be defined by an operational amplifier circuit with series impedances $Z_s$ and feedback impedances $Z_f$.

In this example, series impedances defining transfer functions of each sensing circuit 409a and 409b is $Z_{s1}$ and $Z_{s2}$ respectively.

In this example also, feedback impedances defining transfer functions of each sensing circuit 409a and 409b are $Z_{f1}$ and $Z_{f2}$ respectively.

In this example, $V_{u1}$ and $V_{u2}$ represent the signal at the inputs 426a and 426b of the sensing circuits 409a and 409b respectively.

Considering the unknown series impedances:

$$V_{in} - V_{u1} = I_{u1} Z_{u1} \quad 30$$

$$V_{in} - V_{u2} = I_{u2} Z_{u2} \quad 31$$

where $V_{u1}$ and $V_{u2}$ are the voltages at the inputs 426a and 426b after the unknown series impedance, and $i_{u1}$ and $i_{u2}$ are the currents 428a and 428b flowing through the unknown impedances and into the sensing circuits 409a and 409b.

Now the sensing device can be generalised by using a transfer function matrix TF1 and TF2 for each measurement circuit respectively 409a and 409b:

Consider the circuit of FIG. 12, representing a general form of sensing circuitry of various embodiments of the invention.

Considering the unknown series impedance represented by the electrode-surface interface.

$$V_{in} - V_{u1} = I_{u1} Z_{u1} \quad 32$$

$$V_{in} - V_{u2} = I_{u2} Z_{u2} \quad 33$$

Where $V_{u1}$ and $V_{u2}$ are signals at the outputs of the first and second electrodes with unknown series impedance represented as $Z_{u1}$ 425a and $Z_{u2}$ 425b, $i_{u1}$ and $i_{u2}$ are the currents flowing through the same unknown impedances into the sensing circuitry at inputs 426a and 426b. Equations 34 to 37 deliberately omitted.

Now the sensing device formed of the sensor, with first and second electrodes, and sensing circuitry 409 can be generalised by using a transfer function {TF1, TF2}:

$$V_1 = TF_{1v} V_{u1} + TF_{1i} i_{u1} \quad 38$$

$$V_2 = TF_{2v} V_{u2} + TF_{2i} i_{u2} \quad 39$$

where $V_1$ and $V_2$ are the output voltages, sensing signals or sensing signal channels, at outputs 427a and 427b, which relate linearly to the input voltages and currents at 426a and 426b. We can rewrite this in matrix form:

$$\begin{pmatrix} 1 & 0 & i_{u1} & -1 \\ 0 & 1 & H_{12} i_{u2} & -1 \\ TF_{1v} & 0 & 0 & 0 \\ 0 & TF_{2v} & 0 & 0 \end{pmatrix} \cdot \begin{pmatrix} V_{u1} \\ V_{u2} \\ Z_{u1} \\ V_{in} \end{pmatrix} = \begin{pmatrix} 0 \\ -i_{u2} k_{12} \\ V_1 - i_{u1} TF_{1i} \\ V_2 - i_{u2} TF_{2i} \end{pmatrix} \quad \text{Equation 40}$$

Which can be solved using standard linear matrix techniques:

$$V_{u1} = \frac{V_1 - i_{u1}TF_{1i}}{TF_{1v}} \quad \text{Equation 41}$$

$$V_{u2} = \frac{V_2 - i_{u2}TF_{2i}}{TF_{2v}} \quad \text{Equation 42}$$

$$Z_{u1} = \frac{(-V_1 + i_{u1}TF_{1i})TF_{2v} + TF_{1v}(V_2 - i_{u2}TF_{2i} + i_{u2}k_{12}TF_{2v})}{(i_{u1} - H_{12}i_{u2})TF_{1v}TF_{2v}} \quad \text{Equation 43}$$

$$V_{in} = \frac{H_{12}i_{u2}(-V_1 + i_{u1}TF_{1i})TF_{2v} + i_{u1}TF_{1v}(V_2 - i_{u2}TF_{2i} + i_{u2}k_{12}TF_{2v})}{(i_{u1} - H_{12}i_{u2})TF_{1v}TF_{2v}} \quad \text{Equation 44}$$

We see that the unknown input voltage $V_{in}$ can be estimated by measuring both output voltages and input currents.

The invention will now be illustrated with example embodiments using two-channels, generalized circuit for the receiver circuits, the same signa connection for each channel, and the processor measuring current and voltage.

If both unknown sensor impedances are the same, then:

$$H_{12} \to 1; k_{12} \to 0 \quad \text{Equation 45}$$

$$V_{u1} = \frac{V_1 - i_{u1}TF_{1i}}{TF_{1v}} \quad \text{Equation 46}$$

$$V_{u2} = \frac{V_2 - i_{u2}TF_{2i}}{TF_{2v}} \quad \text{Equation 47}$$

$$Z_{u1} = \frac{TF_{1v}(V_2 - i_{u2}TF_{2i}) + (-V_1 + i_{u1}TF_{1i})TF_{2v}}{(i_{u1} - i_{u2})TF_{1v}TF_{2v}} \quad \text{Equation 48}$$

$$V_{in} = \frac{i_{u1}TF_{1v}(V_2 - i_{u2}TF_{2i}) + i_{u2}(-V_1 + i_{u1}TF_{1i})TF_{2v}}{(i_{u1} - i_{u2})TF_{1v}TF_{2v}} \quad \text{Equation 49}$$

Note that when $H_{12}=1$ and $k_{12}=0$ there is a requirement that:

$$i_{u1} \neq i_{u2} \quad 62$$

which implies a constraint on the circuits that the two input impedances must be different and/or the gains of sensing circuitry 409a and 409b must be different.

Below are illustrated various circuits representing the body, sensor electrodes, and sensing circuits.

The invention will now be illustrated with example embodiments using two-channels, both using inverting amplifiers as receiver circuits, having different impedances for the signal connections, and with the processor reading both voltage and current.

In one embodiment the sensing circuits may be in the class of inverting amplifiers. We can represent this class of circuit with no gain due to input current, and the amplifier gain is given by:

$$TF_{1i} \to 0, TF_{2i} \to 0, TF_{1v} \to -\frac{Z_{f1}}{Z_{s1}}, TF_{2v} \to -\frac{Z_{f2}}{Z_{s2}} \quad \text{Equation 50}$$

$$V_{u1} = \frac{-V_1 Z_{s1}}{Z_{f1}} \quad \text{Equation 51}$$

$$V_{u2} = \frac{-V_2 Z_{s2}}{Z_{f2}} \quad \text{Equation 52}$$

-continued $$Z_{u1} = \frac{i_{u2}k_{12}Z_{f1}Z_{f2} + V_1 Z_{f2} Z_{s1} - V_2 Z_{f1} Z_{s2}}{i_{u1} Z_{f1} Z_{f2} - H_{12} i_{u2} Z_{f1} Z_{f2}} \quad \text{Equation 53}$$

$$V_{in} = \frac{i_{u1} i_{u2} k_{12} Z_{f1} Z_{f2} + H_{12} i_{u2} V_1 Z_{f2} Z_{s1} - i_{u1} V_2 Z_{f1} Z_{s2}}{i_{u1} Z_{f1} Z_{f2} - H_{12} i_{u2} Z_{f1} Z_{f2}} \quad \text{Equation 54}$$

where $Z_{f1}$ and $Z_{f2}$ are in the feedback path for 409a and 409b, and $Z_{s1}$ and $Z_{s2}$ are in the input path.

The invention will now be illustrated with example embodiments using two-channels, both including inverting amplifiers as receiver circuits, using different impedances for the signal connection, and with the processor reading only voltage.

In addition, for an inverting amplifier $$-V_1 + V_{u1} = i_{u1}(Z_{f1} + Z_{s1}) \quad 55$$

$$-V_2 + V_{u2} = i_{u2}(Z_{f2} + Z_{s2}) \quad 56$$

Equations 57 to 60 deliberately omitted.

We can therefore eliminate $i_{u1}$ and $i_{u2}$ from the above equations:

Solving for $V_{in}$:

$$V_{in} = -\frac{V_1 V_2 (k_{12} - H_{12} Z_{s1} + Z_{s2})}{-H_{12} V_2 Z_{f1} + V_1 Z_{f2}} \quad \text{Equation 61}$$

The invention will now be illustrated with example embodiments using two channel, both including non-inverting amplifiers as receiver circuits, having the same impedance for the signal connection and the processor reading only voltage.

In another embodiment the sensing circuits may be in the class of non-inverting amplifiers, when $H_{12}=1$ and $k_{12}=0$.

$$TF_{1i} \to 0, TF_{2i} \to 0, TF_{1v} \to 1 + \frac{Z_{f1}}{Z_1}, TF_{2v} \to 1 + \frac{Z_{f2}}{Z_2} \quad \text{Equation 610}$$

So that the channel transfer functions are $$V_1 = \left(1 + \frac{Z_{f1}}{Z_1}\right) V_{in} \quad \text{Equation 611}$$

$$V_2 = \left(1 + \frac{Z_{f2}}{Z_2}\right) V_{in} \quad \text{Equation 612}$$

The biopotential can be reconstructed from $$V_{in} = \frac{i_{u1} V_2 Z_2 (Z_1 + Z_{f1}) - H_{12} i_{u2} V_1 Z_1 (Z_2 + Z_{f2})}{(i_{u1} - H_{12} i_{u2})(Z_1 + Z_{f1})(Z_2 + Z_{f2})} \quad \text{Equation 613}$$

Note that eliminating $i_{u1}$ and $i_{u2}$ using the full set of equations above is possible $$V_1 Z_1 Z_{s1} = V_{in}(Z_1 + Z_{f1}) Z_{s1} \quad 63$$

$$V_2 Z_2 Z_{s2} = V_{in}(Z_{s2} + Z_{f2}) Z_{s2} \quad 64$$

$$Z_{s1} + Z_{f1} \neq 0 \quad 65$$

$$Z_{s2} + Z_{f2} \neq 0 \quad 66$$

$$Z_{s1} Z_{s2} = 0 \quad 660$$

But the third constraint of Equation 660 is unachievable, even though solutions for Vin exist:

$$V_{in} = \frac{V_1 Z_1}{Z_1 + Z_{f1}} \qquad \text{Equation 67}$$

$$V_{in} = \frac{V_2 Z_2}{Z_2 + Z_{f2}} \qquad \text{Equation 68}$$

However, the biopotential can be reconstructed if the input impedance of a practically implemented operational amplifier is considered.

The invention will now be illustrated with example embodiments having using two channels, one inverting and one non-inverting amplifier, using the same signal connection impedance, and the processor measuring both input current and voltage.

In various other embodiments the sensing circuits are an inverting (circuit 1) and non-inverting (circuit 2) amplifier. Then:

$$TF1_2, TF2_2 \to 0; TF1_1 \to -\frac{Z_{f1}}{Z_{in1}}; TF2_1 \to 1 + \frac{Z_{f2}}{Z_{s2}} \qquad \text{Equation 69}$$

$$V_{u1} = \frac{-V_1 Z_{s1}}{Z_{f1}} \qquad \text{Equation 70}$$

$$V_{u2} = \frac{V_2}{1 + \frac{Z_{f2}}{Z_{s2}}} \qquad \text{Equation 71}$$

$$Z_{u1} = \frac{V_2 Z_2 Z_{f1} + V_1(Z_2 + Z_{f2}) Z_{s1}}{(i_{u1} - i_{u2}) Z_{f1}(Z_2 + Z_{f2})} \qquad \text{Equation 72}$$

$$V_{in} = \frac{i_{u1} V_2 Z_2 Z_{f1} + i_{u2} V_1(Z_2 + Z_{f2}) Z_{s1}}{(i_{u1} - i_{u2}) Z_{f1}(Z_2 + Z_{f2})} \qquad \text{Equation 73}$$

The invention will now be illustrated with example embodiments having two channels, one an inverting amplifier and one non-inverting amplifier, using the same signal connection impedance, and where the processor reads only voltage.

In addition, we know that for a real non-inverting amplifier there is an input impedance:

$$-V_1 + V_{u1} = i_{u1}(Z_{f1} + Z_{s1}) \qquad \text{Equation 74}$$

$$-V_2 \frac{Z_2}{Z_2 + Z_{f2}} + V_{u2} = i_{u2} Z_{s2} \qquad \text{Equation 75}$$

We can therefore eliminate $V_{u1}$, $V_{u2}$ and $Z_u$ from the above equations:

$$i_{u1} V_2 Z_2 + \frac{i_{u2}(Z_2 + Z_{f2})(V_{in} Z_{f1} + V_{s1})}{Z_{f1}} = i_{u1} V_{in}(Z_2 + Z_{f2}) \qquad \text{Equation 76}$$

$$\frac{i_{u1} Z_{f1}(V_2 Z_2 - V_{in}(Z_2 + Z_{f2})) + i_{u2}(Z_2 + Z_{f2})(V_{in} Z_{f1} + V_1 Z_{s1})}{(i_{u1} - i_{u2}) Z_{f1}} = 0 \qquad \text{Equation 77}$$

$$i_{u1} \neq i_{u2} \qquad 78$$

$$Z_{f1} \neq 0 \qquad 79$$

$$Z_2 + Z_{f2} \neq 0 \qquad 80$$

This also removes dependency on $Z_{s2}$ i.e. the input impedance of the non-inverting Op-Amp. The constraints are achievable, and we can find $V_{in}$:

$$V_{in} = \frac{i_{u1} V_2 Z_2 Z_{f1} + i_{u2} V_1(Z_2 + Z_{f2}) Z_{s1}}{(i_{u1} - i_{u2}) Z_{f1}(Z_2 + Z_{f2})} \qquad \text{Equation 81}$$

The invention will now be illustrated with example embodiments having two channels, both differential amplifiers, different impedances for the signal connections of each channel, and where the processor reads only voltage.

In various other embodiments the sensing circuits are differential amplifiers. Then:

$$TF_{1i} \to 0, TF_{2i} \to 0, TF_{1v} \to \frac{(Z_{11} + Z_{31}) Z_{41}}{Z_{11}(Z_{21} + Z_{41})}, \qquad \text{Equation 701}$$

$$TF_{2v} \to \frac{(Z_{12} + Z_{32}) Z_{42}}{Z_{12}(Z_{22} + Z_{42})}, i_{u1} \to \frac{V_1 Z_{11}}{(Z_{11} + Z_{31}) Z_{41}},$$

$$i_{u2} \to \frac{V_2 Z_{12}}{(Z_{12} + Z_{32}) Z_{42}}$$

The channel transfer functions are $$V_1 = \frac{Z_{41}}{Z_{21} + Z_{41}} \frac{(Z_{11} + Z_{31})}{Z_{11}} V_{in} \qquad \text{Equation 82}$$

$$V_2 = \frac{Z_{42}}{Z_{22} + Z_{42}} \frac{(Z_{12} + Z_{32})}{Z_{12}} V_{in} \qquad \text{Equation 83}$$

and the biopotential signal is reconstructed as $$V_{in} = \frac{V_1 V_2 Z_{11} Z_{12}(k_{12} + Z_{22} - H_{12}(Z_{21} + Z_{41}) + Z_{42})}{-H_{12} V_2 Z_{12}(Z_{11} + Z_{31}) Z_{41} + V_1 Z_{11}(Z_{12} + Z_{32}) Z_{42}} \qquad \text{Equation 84}$$

The invention will now be illustrated with example embodiments having multiple-channels, linear transfer functions, different impedances for the signal connection from the body to each channel, and where the processor reads voltage and current.

The transfer function for the sensing circuitry of FIG. 12 with multiple input channels each having a transfer function $$V_n = i_{un} + V_{in} TF_{nv} - i_{un} Z_{un} TF_{nv} \qquad 85$$

where $$Z_{un} = k_{1n} + H_{1n} Z_{u1} \qquad 86$$

can be expressed in matrix form.

$$\begin{pmatrix} TF_{1v} & -i_{u1} TF_{1v} \\ TF_{2v} & -H_{12} i_{u2} TF_{2v} \\ \vdots & \vdots \\ TF_{nv} & -H_{1n} i_{un} TF_{nv} \end{pmatrix} \cdot \begin{pmatrix} V_{in} \\ Z_{u1} \end{pmatrix} = \begin{pmatrix} V_1 - i_{u1} TF_{1i} \\ V_2 - i_{u2} TF_{2i} + i_{u2} k_{12} TF_{2v} \\ \vdots \\ V_n - i_{un} TF_{ni} + i_{un} k_{1n} TF_{nv} \end{pmatrix} \qquad \text{Equation 87}$$

In the embodiment illustrated with reference to FIG. 8, to give one example, the linear relationship between $Z_{u1}$ and $Z_{u2}$ is arranged by first and second signal channels being arranged to form a linear relationship of impedances with the body.

Equations 88 to 94 deliberately omitted.

This equation can be solved using linear algebra known to the reader.

$$\begin{pmatrix} V_{in} \\ Z_{u1} \end{pmatrix} = \begin{pmatrix} TF_{1v} & -i_{u1}TF_{1v} \\ TF_{2v} & -H_{12}i_{u2}TF_{2v} \\ \vdots & \vdots \\ TF_{nv} & -H_{1n}i_{un}TF_{nv} \end{pmatrix}^+ \begin{pmatrix} V_1 - i_{u1}TF_{1i} \\ V_2 - i_{u2}TF_{2i} + i_{u2}k_{12}TF_{2v} \\ \vdots \\ V_n - i_{un}TF_{ni} + i_{un}k_{1n}TF_{nv} \end{pmatrix} \quad \text{Equation 95}$$

In one embodiment a processor similar to 310 determines Vin (the biopotential signal) from $TF_1v$, $TF_2v$, $TF_1i$, $TF_{2i}$, $i_{u1}$, $i_{u2}$, $H_{12}$, $k_{12}$, $V_1$ (first sensor signal), $V_2$ (second sensor channel) using a form of Equation 95 from which $Z_{u1}$ has been algebraically eliminated.

Figure 13:
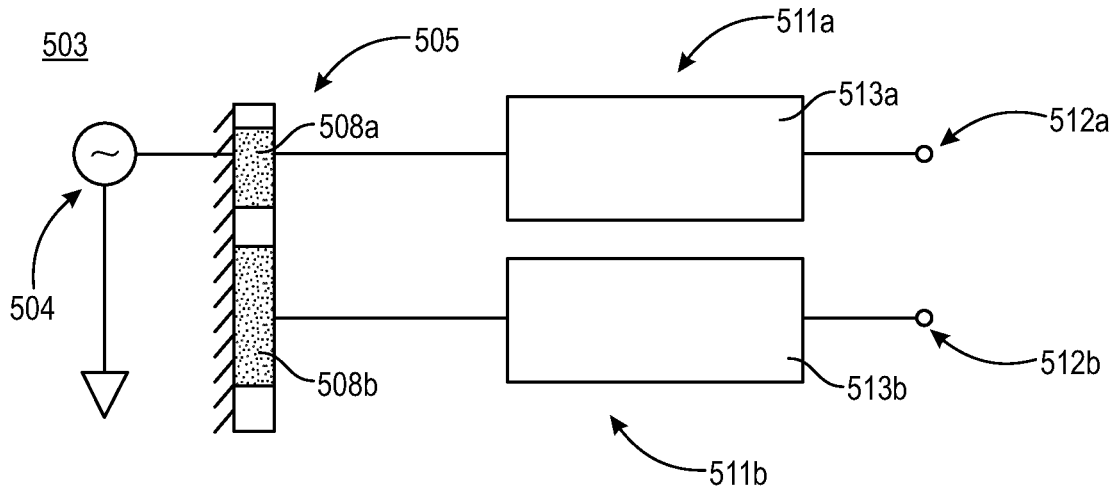
FIG. 13 illustrates a further embodiment of the present invention.

FIG. 13 illustrates two embodiments of the invention. FIG. 13 illustrates generally the problem of capturing a biopotential signal 504 at the surface of a body 503 when the sensor receiver 508 available to form a connection to the body forms a signal connection for the biopotential signal 504 that has an unknown impedance parameter. A first signal channel 511a is provided to receive a signal at a first channel output. However, a first transfer function of the first channel will depend on the unknown impedance parameter, referred to here as the unknown first impedance parameter. The impedance parameter may be an unknown resistance or reactance, a component of these or a combination of these. For example, the sensor receiver 508 may form a signal connection with an unknown impedance parameter formed by a resistance in parallel with a capacitance. The first transfer function will also depend on parameters of an circuit 513a with its own transfer function and with known component values. In one example this apparatus may be a charge amplifier with known series and feedback component parameters.

The signal at the first channel output may be expressed as $$V_1 = f1(V_{in}, Z_{u1}) \quad 96$$

where $V_{in}$ is the biopotential signal, $Z_{u1}$ is the unknown first impedance parameter and f1 is the transfer function. V1 depends on the first unknown impedance parameter and therefore cannot be determined.

FIG. 13 shows a second signal channel 511b arranged to capture the same biopotential signal 504. The second channel 511b has a second transfer function and a second signal output. The second transfer function of this embodiment also depends on the first unknown impedance parameter by receiving the biopotential signal via an electrode 508b that forms a signal connection with an unknown impedance parameter that is defined by a known relation to the unknown impedance parameter signal connection of the electrode 508a. The second transfer function also depends on a transfer function of a second channel circuit 513b.

The first and second signal channels 511a and 511b therefore share the same unknown first impedance parameter.

This allows the system to be described by a set of two relations, or equations, for the biopotential signal dependent on each signal channel dependent and on the unknown first impedance parameter. A solution can then be found for the bipotential signal 504.

Therefore the embodiment of FIG. 13 provides a sensor device having a sensor receiver 508 that forms a signal connection for the biopotential signal 504 with a first signal channel 511a and a second signal channel 511b where the system can be describes as a set of mathematical relations which depend on the firsts transfer function of the first signal channel, or the transfer function of the apparatus 513a, which also depend on the second transfer function of the second signal channel 511b, and which also depends on the first unknown impedance parameter.

As discussed above the first and second signal channels share the same first unknown impedance parameter. In the embodiment shown in FIG. 13 this sharing is achieved with a sensor receiver 508 which has first and second sensor electrodes 506a and 506b which each form part of the first and second signal channels respectively along with first and second channel circuits which each have a known transfer function and known components which form the respective transfer functions. In this embodiment the electrodes have a known relationship for unknown impedance parameters. This is, the unknown second impedance parameter can be defined by a known relation dependent on the unknown first impedance parameter. Therefore, the system has a first unknown impedance parameter Zu1 which is associated with the electrode of the first signal channel 511a and second unknown impedance associated Zu2 with the second signal channel 511b. Here, the second transfer function of the second signal channel 511b has been arranged to depend specifically on an unknown second impedance parameter which has a known relationship with the unknown first impedance parameter.

Figure 14:
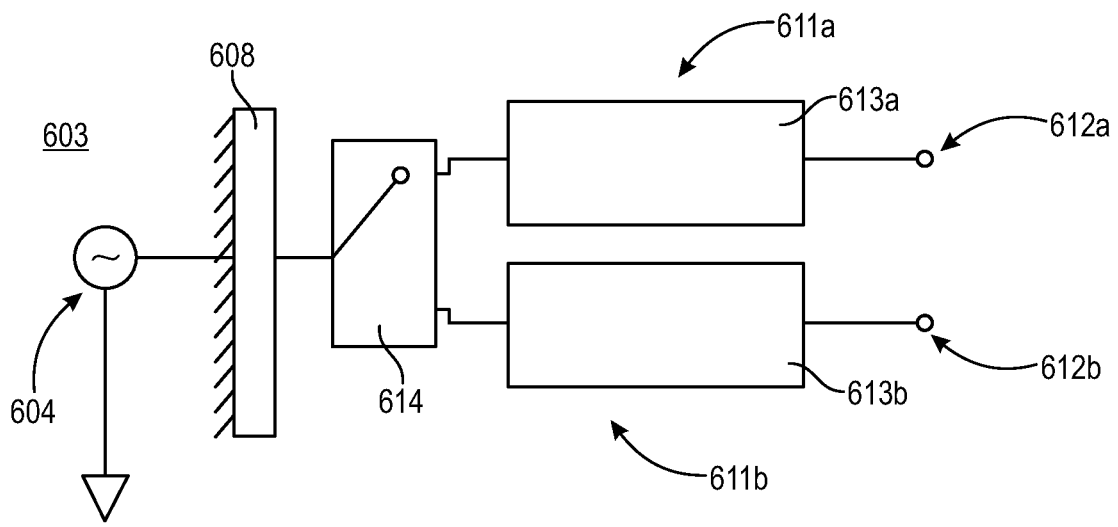
FIG. 14 illustrates another embodiment of the present invention.

As discussed above, the first and second signal channels share the same first unknown impedance parameter. FIG. 14 shows an alternative embodiment which archives the first and second signal channels sharing the same first unknown impedance parameter by providing first and second signal channels 611a and 611b including the same sensor electrode 608. In this embodiment the same electrode 608 is connected via a switch 614 which switches between devices 613a and 613b to connect the sensor receiver 608 and electrode 608 alternately to form part of the first signal channel 611a and part of the second signal channel 611b.

In overview with respect to the embodiments of FIG. 13 and FIG. 14, the original biopotential and the unknown impedance can be conceptualised as two unknown variables: an unknown input and unknown impedance parameter, respectively. A measurement channel can be described with an equation that relates the unknown input, unknown parameter and measured (therefore, known) output. By itself, this is a system of two unknowns and one equation, which cannot be solved (Equation 96).

Introducing a second signal channel introduces the corresponding number of equations, or relations for the biopotential signal; so two signal, or measurement, channels allows a solution (two equations, two unknowns), as long as the unknown impedance parameter is shared by both measurement channels.

$$V_2 = f2(V_{in}, Z_{u2}) \quad 97$$

This sharing of the parameter can be achieved in at least two ways:

1. A second unknown impedance can be related by a known factor to the first unknown impedance e.g.

$$Z_{u2} = nZ_{u1}; V_2 = f2(V_{in}, Z_{u1}) \quad 98$$

2. We can switch between the two measurement channels, while keeping the same unknown impedance e.g.

$$V_2 = f2(V_{in}, Z_{u1}) \quad 99$$

It is important that the equation corresponding to the second measurement channel cannot reduce to the equation corresponding to the first measurement channel. In the case of the measurement circuits proposed, this is achieved because output voltages are non-linearly related to unknown impedance:

$$V_1 = \frac{G\, V_{in}}{Z_1 + Z_{u1}} \qquad \text{Equation 100}$$

where G and Z are parameters known from chosen electrical component values.

Further and additional embodiments of the invention will now be illustrated.

Embodiments of the invention provide an apparatus which generates a reconstructed biopotential signal sensed at a surface of a body using a sensor device which address a problem of impedance of signal connections between a body and a sensor device having unknown and/or variable impedance by providing two or more channels between the body and outputs for a processor where the channels each have a transfer function which the impedance through a sensor device and an interface between the body and the sensor device where the channels are arranged so that the unknown and/or variable impedance of one channel is related to the unknown and/or variable impedance of the other channel by a linear defined relationship and where the channels provide two or more transfer functions for an assumed same biopotential signal to two or more signal outputs for the processor so that operations equivalent to equating analytic expressions of the transfer functions and substituting one unknown and/or variable impedance for the other will eliminate the unknown and/or variable impedances and will allow the biopotential signal to be reconstructed independently of artefacts of the body-sensor interface or sensor. Biopotential signals can be captured with a variety of artefacts mitigated and/or eliminated. Such artefacts may be caused by a variation between given implementations in the capacitive and/or resistive impedance of the body-sensor interface, such as might result by different materials being between a body and a sensor or by different sensors as required for given applications. Such artefacts may be caused by variations in the capacitive and/or resistive impedance over time, such as caused by movement of a body or movement of the sensor relative to the body. Such artefacts may be caused by capacitive (imaginary) impedance, resistive (real impedance) or real and imaginary (complex impedance). In some embodiments the relationship of sensor impedances of respective channels may be arranged by two distinct sensor electrodes and differing properties of those or the arrangement of electrode and body interface. In some embodiments the relationship of sensor impedances of respective channels may be arranged by a single electrode with a connection switched between two or more channels.

The reader will appreciate that impedance is frequency dependent.

The reader will appreciate that various of the above equations contain variables in the frequency domain.

In various embodiments more than two sensor electrode pathways can be solved in a least-squares sense, or by other or other optimisation known to the reader, by adding rows to the above matrix equation.

In various embodiments an electrode is used to provide a first signal connection to receive a biopotential signal from the body and a receiver circuit to provide a first signal channel comprising the signal connection combined with the receiver circuit where a first analytic expression will define the biopotential signal dependent on an impedance of the first signal connection, on impedances of the receiver circuit and on outputs of the receiver circuitry.

In various embodiments an electrode is used to provide a second signal connection to receive the same biopotential signal from the body and a receiver circuit to provide a second signal channel comprising the signal connection combined with the receiver circuit where a second analytic expression will define the biopotential signal dependent on an impedance of the second signal connection, on impedances of the receiver circuit and on outputs of the receiver circuitry.

In various embodiments the electrodes are arranged to provide a defined expression relating the impedance of the first and second signal connections.

In various embodiments the biopotential signal can be determined using an expression which is derived by operations on the first analytic expression, the second analytic expression and the impedance expression, wherein the operations eliminate the impedance of the first and second signal connections.

In various embodiments the operations comprise steps equivalent to using the impedance expression to eliminate the impedance of the second signal connection.

In various embodiments the operations comprise steps equivalent to equating the first and second analytic expressions.

In various embodiments the operations may comprise equivalent Gaussian elimination.

The outputs of a receiver circuit may be voltages and/or currents and/or voltages representing currents.

In various embodiments a sensing processor may stand-alone from the sensing circuitry and may not have a direct electrical connection to the sensing circuitry. In some of these embodiments signals from the sensing circuitry may be transmitted to the sensing processor. In other embodiments sensing circuitry may be operable to store signals on a readable medium which is readable by the sensing processor.

In various embodiments determining the biopotential signal independently of an impedance between the surface of the body and a sensor receiver, with first and second electrodes, relies on a defined relationship between approximations of real capacitive sensors. For example, the defined relationship may be for electrode area with a real sensor forming a capacitance between first and second electrodes and a surface of a body may be approximated as first and second capacitors. The reader will appreciate that this or similar approximations will mitigate the effect of changes in capacitances between the sensor receiver and the surface of a body. This is particularly but not exclusively where a given effect for capacitance apply to each capacitance formed between the surface and an electrode.

In various embodiments of the invention a sensor receiver may be substituted for one or more signal pick-ups. In various embodiments the one or more signal pick-ups may be formed of one or more elements.

In various embodiments electrodes used to capture biopotential signals may be provided by multiple elements providing the function of the sensor receiver illustrated.

In various alternative embodiments of the invention a multiple electrode sensing pick-up, such as the multiple electrode element illustrated with reference to FIG. 8 may have more than two electrodes.

In various alternative embodiments of the invention a multiple electrode sensing pick-up, such as illustrated with reference to FIG. 8, may have two or more electrodes which provide impedances for the biopotential signal that differ according to a defined relationship other than a factor of each other. In various embodiments the relationship of impedances of electrodes of a sensor receiver may be as defined by any suitable expression known to the reader, including factors, or polynomials.

In various embodiments, alternative to that illustrated with reference to FIG. 8, the impedance provided by an electrode may be resistive. One or more electrodes of these embodiments may make a direct electrically conductive connection with the surface of the body.

In various embodiments, alternative to that illustrated with reference to FIG. 8, the impedance provided by an electrode may be inductive.

In various embodiments, alternative to that illustrated with reference to FIG. 8, the impedance provided by an electrode may a resistance.

In various embodiments, alternative to that illustrated with reference to FIG. 8, the impedance provided by an electrode may be reactance.

In various embodiments, alternative to that illustrated with reference to FIG. 8, the impedance provided by an electrode may be resistance and a reactance.

In various embodiments a channel for a signal may be a channel for a data signal. In various embodiments a data signal may be a transmitted data signal. In various embodiments a data signal may be a stored data signal. A data signal may be a digitised signal derived from an analogue signal.

Figure 11:
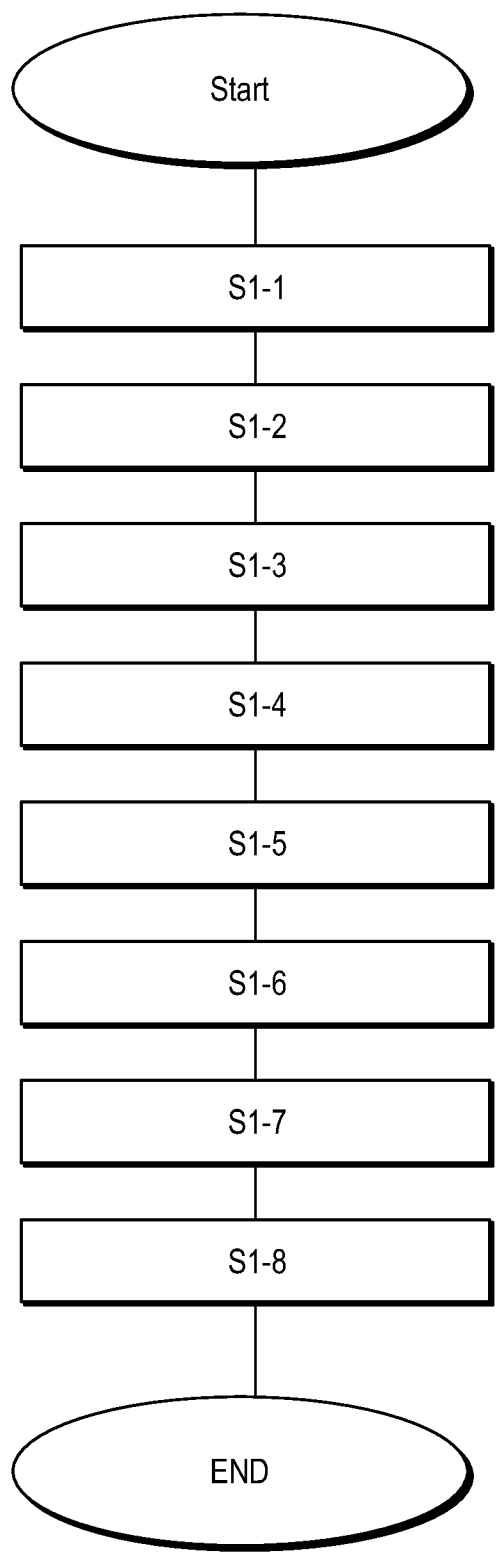
FIG. 11 illustrates a process performed by a sensing processor of the embodiment of FIGS. 8 and 9 or the embodiment of FIG. 10.

In various embodiments any combination of individual steps illustrated with reference to FIG. 11 are taken.

In various alternative embodiments acquired signals are stored in a non-volatile memory of the processor.

In various alternative embodiments acquired signals are stored using a processor and/or computer readable medium.

In various embodiments first and second sensing signals output from sensing circuitry may be provided as first and second channels of a sensing signal. In various embodiments the sensing signals output by sensing circuitry or used by a sensing processor may be analogue signals. In other embodiments the sensing the sensing signals output by sensing circuitry or used by a sensing processor may be digitally encoded signals.

In various embodiments a sensor provides a connection at a surface of the body. In various embodiments the connection is a connection for a signal. In some embodiments the sensor provides a capacitive connection. In various embodiments the sensor provides a conductive connection. In various embodiments the sensor provides an inductive connection.

Various embodiments have sensors which provide any connection known to the reader suitable to allow the sensing device to receive a biopotential signal. The reader may recognise the sensing connection as a pick-up connection.

In various embodiments a biopotential signal is sensed as a signal which has one of more characteristics of an electrical signal within the body or available at the surface of the body. In various embodiments a biopotential signal may be a voltage signal.

In various alternative embodiments the first and second electrodes may have inductances which contribute to a defined relationship of impedances.

Some embodiments of the invention provide a capacitive connection for a biopotential signal to the surface of a body that may have advantages over a direct resistive or conducting connection. In one example an advantage of longevity of connection is provided. On one specific example an advantage of longevity is achieved when a sensor is required to be located on, or affixed to, the skin of a biological subject. In a specific example again, the sensor can be affixed by a biologically compatible adhesive, or other affixing or locating means, that is not required to be conductive. However, a capacitive connection with a known and stable capacitance is difficult to achieve. One effect that may vary capacitance is a variation of the air gap between a sensor receiver and the surface of the body. This variation may be spatially over a sensing region or periodically and temporally with movement or contortion of the subject or temporally with degradation of adhesives, for example, used to affix the sensor to the subject. These effects are particularly apparent with a biological subject.

In various embodiments an adhesive used to adhere the sensor to a surface, such as skin is arranged on the sensor between the sensor and the surface to adhere the sensor directly. In other embodiments a layer of adhesive material may be arranged on an opposite side of the sensor to the surface and extending beyond the sensor to adhere to the surface and hold the sensor at the surface.

The reader may recognise a capacitive connection provided by sensors as an electrostatic connection. The reader may recognise a resistive connection as a galvanic connection.

In various additional embodiments it is not essential that the impedances formed by first and second sensor electrodes with the body precisely fit a defined relationship. In these embodiments, variations from a defined relationship may cause an error in a biopotential signal determined. In various applications varying degrees of effort may be acceptable as will be apparent to the reader.

In various embodiments processes implemented to carry out operations illustrated above using mathematical or algebraic expressions, relations, relationships or equations, by performing computational or data operations on data or code carrying information describing the algebraic expressions, relations, relationships or equations.

In various embodiments processes implemented to carry out operations illustrated above using mathematical or algebraic expressions, relations, relationships or equations, by performing any suitable computational or data operations known to the reader such as, to name some examples only, read, write erase, polling, floating point operations, scalar, vector or matrix operations such as multiplication, and addition.

In some embodiments, first and second sensor receivers share an electrode. The electrode may form a capacitive connection for the biopotential signal. Alternatively, the electrode may form a conductive connection for the biopotential signal. Alternatively, the electrode may form a combination capacitive and conductive connection for the biopotential signal.

In the preceding description and the following claims, the word "comprise" or variations thereof is used in an inclusive sense to specify the presence of the stated feature or features. This term does not preclude the presence or addition of further features in various embodiments.

In the preceding description and the following claims, the word "a" is not intended to exclude "another" "a second", a "plurality" or similar expressions.

As used herein the term 'capture' refers broadly to capturing a signal or data which carries information on the biopotential signal, and may include, to name examples, generating a signal and generating data carrying information on a signal.

As used herein the term 'electrode' refers broadly to a conductor through which electricity enters or leaves a circuit, wire, rail, channel, object, substance, or region and explicitly includes cases where the electricity enters or leaves by conductive connections formed by the conductor and/or capacitive connections formed by the conductor.

As used herein the term 'parameter' refers broadly to any numerical or other measurable factor forming one of a set that defines a system or sets the conditions of its operation, and may for example refer to impedance, resistance, reactance, any combination of these.

As used herein the term 'channel' refers broadly to a path for an electric signal.

As used herein the term 'relation' refers broadly to anything which defines relationships between values or parameters and a relation may be expressed in text, data, matrices, vectors, tables and data, media or memory carrying information on these.

As used herein the term 'dependent on', 'depends on' or similar used in reference to a parameter or value, for example, and a relation or expression refers to the parameter or value being a variable in the relation or expression. For example a As used herein the term 'biopotential signal' refers broadly to an electrical signal measures at, on or in biological bodies, and includes electrical signals (voltages) that are generated by physiological processes occurring within the body.

As used herein the term 'sensing' refers broadly to detecting and identifying a signal and characteristics of the signal such as parameters which define the signal over time to give an example.

As used herein the term 'impedance parameter' in reference to some embodiments may refer to impedance or may refer for some embodiments to an electronic parameter such as capacitance or resistance on which impedance depends.

In various embodiments "transfer function" may be transfer functions mapping one input to one output, one input to many outputs, many inputs to many outputs or any collocation or combination of these. To give a specific example a transfer function may be defined for a single biopotential signal to first and second outputs. To give another specific example a transfer function may be defined for first input to a first output and a second input to a second output.

As used herein "electrode impedance" or "sensor impedance", are intended to refer broadly to an impedance between the signal of interest and the sensor or electrode and includes, for example, the impedance formed by a capacitance formed between a surface and a given electrode separated by a layer of dielectric material and/or an air gap.

In various embodiments "circuitry" refers broadly to various suitable electronics with structure as illustrated or to perform functions as illustrated and these may include analogue circuits, digital circuits, microcontrollers, programmable logic arrays, processors, integrated circuits, Field Programable Gate Arrays or Application Specific Integrated Circuits and virtual machines and includes configurable or programable components with suitable configuration or programming code.

In various embodiments the term "processor" refers broadly to any system or device operable to provide the functionality illustrated or preform steps or processes illustrated and include analogue circuits, digital circuits, microcontrollers, programmable logic arrays, processors, integrated circuits, Field Programable Gate Arrays or Application Specific Integrated Circuits and virtual machines and includes configurable or programable components with suitable configuration or programming code.

In various embodiments a signal is 'captured' by being 'reconstructed' from a received signal, parameter values and expressions.

Various embodiments of the invention are implemented as machine readable code and/or data stored using machine readable media and operable when read to configure a machine to provide structures illustrated or to perform steps or processes illustrated. In various embodiments the machine-readable media may include semi-permanent media, any computer or processor accessible storage, volatile and non-volatile memory.

In various embodiments a sensor has a third electrode. In various embodiments the third electrode is arranged to have a sensor impedance defined by a relation dependent on the impedance of one or both of the first and second electrodes. For example, the following expression for $V_{in}$ may be referred to as dependent on the variables appearing in the expression and/or in expressions making up part of the expression for $V_{in}$.

$$V_{in} = \frac{i_{u1} V_2 Z_2 (Z_1 + Z_{f1}) - H_{12} i_{u2} V_1 Z_1 (Z_2 + Z_{f2})}{(i_{u1} - H_{12} i_{u2})(Z_1 + Z_{f1})(Z_2 + Z_{f2})}.$$

In various embodiments relations are implemented as equations, vector equations, vector relations, matrix relations, and data and/or code and/or tables and/or schema implementing these and any of these may be referred to as a relation or set of relation in given illustrations of the various embodiments.

In various embodiments an unknown impedance parameter may be an unknown electronic parameter such as capacitance, resistance or inductance on which impedance depends. In various embodiments an unknown impedance parameter may be a real or imaginary component of an electronic parameter such as capacitance, resistance or inductance on which impedance depends.

In various embodiments an unknown impedance parameter may be an impedance, resistance or reactance. In various embodiments an unknown impedance parameter may be a real or imaginary component of impedance, resistance or reactance.

In some embodiments a sensor receiver may be formed of one or more sensor electrodes and a one or more terminals to connect a signal received at an electrode to sensing circuitry. In some embodiments a sensor receiver may be formed additionally of a means, such as an adhesive layer or strap, to locate the electrode in relation to a surface of a body. In some embodiments a sensor receiver may be formed additionally of dielectric material located in use between one or more of the electrodes and a surface of a body.

The reader will appreciate that the receiving the biopotential signal at various points or outputs in apparatus such as sensors and circuits is not limited to the 'biopotential signal' being unaffected by the apparatus.

For example a biopotential signal may be received by a sensor electrode, received by a receiver circuit and received at an output of the receiver circuit before being reconstructed by a processor, and the reader will appreciate that reference to 'biopotential signal' does not imply that the biopotential signal is unaltered between the input of the electrode and output of the circuit.

In one embodiment the present invention provides a process of capturing a biopotential signal at a surface of a body using a sensor receiver which forms a first signal connection with the body wherein one or more parameters of impedance of the first signal connection are unknown, the process comprising:

receiving the biopotential signal at an output of a first signal channel having a first channel transfer function which is dependent on the one or more unknown first impedance parameters;

receiving the biopotential signal at an output of a second signal channel having a second channel transfer function dependent on the one or more unknown first impedance parameters;

solving a set of relations to determine the captured biopotential signal wherein the set of relations is defined dependent on:

i) the first channel transfer function,
ii) the second channel transfer function, and
iv) outputs of the first and second signal channels.

The second channel transfer function may be dependent on the first unknown impedance parameter by being dependent on a second impedance parameter which has a known relation to the unknown first impedance parameter defining a dependence on the unknown first impedance parameter.

The known relation of the unknown second impedance parameter to the unknown first impedance parameter may be an approximation.

The derived set of relations may comprise a first relation which relates the biopotential signal to an expression which is dependent on the output signal of the first signal channel, the unknown first impedance parameter and one or more known parameters for components included in the first signal channel.

The derived set of relations may comprise a second relation which relates the biopotential signal to an expression which is dependent on the output signal of the second signal channel, an unknown second impedance parameter and one or more known parameters for components included in the second signal channel.

The unknown second impedance and one or more known parameters for components included in the second signal channel may be selected such that the second relation does not reduce to the first relation.

The derived set of equations may comprise a third relation which relates the unknown second impedance parameter to unknown first impedance parameter.

The first signal channel may be arranged to have a transfer function which is non-linear with respect to the unknown first impedance parameter.

The second signal channel may be arranged to have a transfer function which is non-linear with respect to the unknown first impedance parameter.

The first signal channel may comprise the sensor receiver and a first-channel circuit having a first known transfer function wherein the first channel transfer function is dependent on known component parameters of the first circuit. The first channel transfer function may be determined by electronic parameters of the first signal connection and known electronic parameters of the first circuit. For example, the first channel transfer function may be the transfer function of a circuit formed by the sensor receiver connected to the first apparatus, where the component parameters of the first circuit are known. Also, a relation for the biopotential signal may be dependent on the first channel transfer function and the output of the first channel wherein the first channel transfer function may be dependent on known component parameters of the first channel-circuit and the first unknown impedance parameter of the first signal connection. The first channel transfer function may also be dependent on any known component parameters the sensor receiver. To give an illustrative example, the sensor receiver may have a known resistance and may form a capacitive connection with the body for the biopotential signal of unknown capacitance.

The second signal channel may comprise the sensor receiver and a second channel-circuit having a second known transfer function wherein the second channel transfer function is dependent on known component parameters of the second channel circuit. The second channel transfer function may be determined by electrical parameters of the sensor receiver and/or the signal connection it forms with the body and also by known electrical parameters of the second apparatus.

The process may comprise switching a connection from the first sensor receiver alternately to i) the first-channel circuit to provide a first channel transfer function and to ii) the second-channel circuit to provide a second channel transfer function.

Alternatively, the first sensor receiver may comprise: a first sensor electrode operable to form a first signal connection to receive the biopotential signal, wherein the first sensor electrode is connected to the first-channel circuit to provide the first signal channel and wherein the first sensor receiver; and a second sensor electrode operable to form a second signal connection for to receive the biopotential signal, wherein the second sensor electrode is connected to the second-channel circuit to provide the second signal channel, and wherein the second sensor electrode is arranged such that the second signal connection has an unknown second impedance parameter which has a known relation to the unknown first impedance parameter.

The second signal channel may comprise a second sensor receiver which forms a signal connection with the body having an impedance which is a known relation with an unknown impedance of the signal connection formed by a first sensor receiver of the first signal channel.

The first sensor receiver may comprise a first sensor electrode which forms a signal connection with the body for the biopotential signal and the second sensor receiver may comprise a second sensor electrode which forms a second signal connection with the body for the biopotential signal and the second sensor electrode may be arranged to form a signal connection with an impedance which has a known relation to the impedance of the signal connection formed by the first sensor electrode.

The second sensor electrode may have an electrode area arranged to form a signal connection with an impedance which has a known relation to the impedance of the signal connection formed by the first sensor electrode.

The sensor receiver may have a surface arranged to form a signal connection formed by the second electrode with an impedance which has a known relation to the impedance of the signal connection formed by the first sensor electrode.

The electrode surface may be arranged to provide a resistance which forms a signal connection with an impedance which has a known relation to the impedance of the signal connection formed by the first sensor electrode.

The sensor receiver may comprise one or more conductive layers located between one or more of the first and second the second electrodes and the body in use wherein the one or more conductive layers are arranged so the second sensor receiver forms a signal connection with an impedance which has a known relation to the impedance of the signal connection formed by the first sensor electrode.

The sensor receiver may comprise one or more dielectric layers located between one or more of the first and second the second electrodes and the body in use wherein the one or more dielectric layers are arranged so the second sensor receiver forms a signal connection with an impedance which has a known relation to the impedance of the signal connection formed by the first sensor electrode.

The second signal channel may share the unknown impedance parameter with the first signal channel by the second signal channel sharing with the first signal channel an electrode to share the unknown impedance parameter and the process may switch between first and second signal channels.

In one embodiment the present invention provides a device operable to capture a biopotential signal at a surface of a body using a sensor receiver which forms a first signal connection with the body wherein one or more parameters of impedance of the first signal connection are unknown, the device comprising:
a first signal channel having a first channel transfer function which is dependent on the one or more unknown first impedance parameters;
a second signal channel having a second channel transfer function which is dependent on the one or more unknown first impedance parameters;
a processor operable to solve a set of relations to determine the captured biopotential signal wherein the set of relations is defined dependent on:
i) the first channel transfer function,
ii) the second channel transfer function, and
iv) outputs of the first and second signal channels.

The second channel transfer function may be dependent on the first unknown impedance parameter by being dependent on a second impedance parameter which has a known relation to the unknown first impedance parameter.

Embodiments of the present invention provide a sensing device for sensing biopotential signals in a sensing region at a surface of a body, the sensing device comprising:
first and second input terminals for connection to first and second sensor receivers which each connect the biopotential received at the surface of the body to a respective receiver terminal, wherein a second sensor receiver has a second receiver impedance for the biopotential signal which has a defined relationship with the receiver impedance of the first receiver;
sensing circuitry operable to connect to first and second electrodes to receive first and second electrode signals and to apply a defined transfer function to the first and second electrode signals to output first and second sensing signals; and
a sensing processor operable to determine the biopotential signal dependent on the first and second sensing signals, dependent on parameters of the defined transfer function and dependent on the defined relationship of the first and second sensor impedances.

The defined transfer function may comprise a first channel transfer function applied between a first electrode signal and a first output signal and a second channel transfer function applied between a second electrode signal and a second output signal.

In one embodiment a sensor receiver may comprise one or more capacitive electrodes operable to provide a capacitive connection for the biopotential signal at the surface of the body.

One embodiment may provide a sensor receiver may comprise one or more conductive electrodes operable to provide a conductive connection for the biopotential signal at the surface of the body.

The first and second sensor receivers may comprise respective first and second electrodes each providing a connection for the biopotential signal.

Alternatively, the first and second sensor receivers may have an electrode common to both receivers. The first and second receivers may comprise respective first and second sensor rails each connected between the common electrode and a respective first and second receiver terminal to provide a connection for the first and second input terminals of the sensor device.

The sensing processor may be operable to determine the biopotential signal using operations defined by a matrix expression for i) transfer functions of the sensing electronics, ii) the first and second signal voltages. The expression may be simplified by substitution of impedance of a second sensor electrode using the known relationship to the impedance of the first sensor electrode.

Embodiments of the present invention provide a sensor operable to sense a potential signal in a sensing region at a surface of a body with first and second electrodes which form first and second connections for the potential signal wherein the impedance of the second connection is defined relative to the impedance of the first connection. The sensor may provide outputs for the potential signal sensed in the sensing region via first and second impedances capable of being related by a defined expression.

Embodiments of the present invention provide a sensing electronic device operable to receive a potential signal from a body via first and second connections and operable to provide first and second sensing outputs with defined channel transfer functions between each connection and a respective output. The sensing electronic device may be connected to receive a potential signal via first and second connections having a defined relationship.

Embodiments of the present invention provide signal-determining electronics operable to receive first and second sensing signals provided by sensing electronics with known parameter values defining a first and second transfer functions provided by the sensing electronics for first and second signals received from first and second electrodes of the sensor and operable to determine a potential signal dependent on: the first and second sensing signals; parameters defining first and second transfer functions and dependent on a defined relationship of impedances seen by the potential signal at the first and second electrodes of the sensor.

Embodiments of the present invention provide a sensing device for sensing a potential signal at a surface of a body wherein the sensing device comprises first and second electrodes which each form a connection for the signal with the body and wherein the connection with the body formed by the second electrode differs approximately by a defined relationship from the impedance formed by the first electrode with the body. The relationship may be a factor. The factor may be an integer.

Embodiments of the invention provide sensing circuitry for sensing a potential signal at a body via a sensor which forms a connection with the body wherein the sensing electronics comprise a charge amplifier having a series impedance capable of connection between a sensor and an input of an operational amplifier and having a feedback impedance for the operational amplifier. The series impedance may be arranged to differentiate the potential signal. The feedback impedance may be arranged to integrate the potential signal.

The sensing circuitry may comprise a first charge amplifier to receive at a first input an electrode signal from a first sensor electrode which is operable to form a connection for a biopotential signal and to provide at a first output a first sensing signal and may comprise a second charge amplifier operable to receive at a second input a second electrode signal from a second electrode which is operable to form a connection for a biopotential signal and to provide at a second output a second sensor signal.

The first sensor signal may be the result of a first defined transfer function applied to the first electrode signal. The first transfer signal may be defined by a feedback impedance of the charge amplifier circuit and a series impedance in series with an operational amplifier input. A feedback impedance may be defined by a capacitor and a resistor connected to define an integrating function for the charge amplifier. A series impedance operable to define a differentiation function at the input of the charge amplifier.

The second sensor signal may be the result of a second defined transfer function applied to the second electrode signal. The second transfer signal may be defined by a feedback impedance of the charge amplifier circuit and a series impedance in series with an operational amplifier input. A feedback impedance may be defined by a capacitor and a resistor connected to define an integrating function for the charge amplifier. A series impedance may be operable to provide a differentiation function at the input of the charge amplifier.

This allows a determination of the potential signal received via the first and second electrodes to be determined dependent on the first and second charge amplifier output signals and component values for respective first and second charge amplifier circuits but independent of the impedance of the connection formed by the first electrode and the body.

The potential signal may be determined independent of the impedance formed by the first electrode with the body by using an expression for the biopotential signal derived by equating expressions for the potential signal dependent on second charge amplifier output signals and component values of respective first and second charge amplifier circuits and by substituting the impedance formed by the second electrode and the body for the product of the sensor factor and the impedance formed by the first electrode with the body.

This determination may be made by data operations which depend on an expression for the biopotential signal received at first and second electrodes having a known relationship of impedances and dependent on the first and second sensor signals using wherein the expression is derived from an analytical expression for current at the inputs of the operational amplifier for a first analytical circuit comprising the first charge amplifier and first sensor electrodes connected at the first input, an analytical expression for impedance derived from conservation of current at a node of the operational amplifier of a second analytical circuit comprising the second charge amplifier and second sensor electrode connected at the second input of charge amplifier circuit and an analytical expression for impedance formed by the second sensor electrode as a function of the impedance formed by the first sensor electrode.

The expression may be derivable using expressions for Kirchhoff's laws for current at a node at the input of an operational amplifier. The expressions may assume an ideal operational amplifier.

In one embodiment the invention provides a sensor receiver operable to receive a potential signal in a sensing region at a surface of a body the sensor receiver having a first electrode and a second electrode to form first and second sensing connections in the sensing region to receive the potential signal wherein the electrodes are arranged such that the second connection has an impedance which approximately relates an impedance of the first connection by a defined relation. The defined relation may be a factor. The defined relation may be a fraction.

The first and/or second electrode may be arranged to form a resistive connection with the body for the potential signal.

The first and/or second electrode may be arranged to form a capacitive connection with the body for the potential signal.

In another embodiment the invention provides a sensor operable to receive a potential signal in a sensing region at a surface of a body the sensor receiver operable to receive the biopotential signal in the sensing region, wherein the sensor comprises first and second signal pathways to first and second receiver terminals to provide the biopotential signal received to sensing electronics wherein the second pathway has an impedance which approximately relates an impedance of the first connection by a defined relation.

In another embodiment the invention provides sensor circuitry for a potential signal received at a body by a sensor receiver over an unknown and/or variable impedance, the sensor circuitry comprising first and second output channels for first and second output signals each signal comprising an amplification of the potential signal wherein the amplification is defined by the gain of an operational amplifier with a feedback impedance and with an input impedance wherein the input impedance is comprised of said unknown and/or variable impedance and a series impedance between the sensor receiver and the operational amplifier. The amplification may be negative. The amplification may be positive. The amplification may be a gain with an absolute value of greater than one. The amplification may be a gain with an absolute value of one. The amplification may be a gain with an absolute value of less than one.

The amplification may be provided by operational amplifier circuits having feedback and series components.

Alternatively, the amplification may be provided by a transfer function module providing amplification as defined by feedback and series component values of an operational amplifier.

In another embodiment the invention provides sensor circuitry operable to determine a potential signal received at a body by a one or more electrodes forming an unknown and/or variable impedance the sensor circuitry comprising first and second output channels for first and second output signals the transfer function of the potential signal to output signals defined by the first and second unknown and/or variable sensor impedances and known component values, wherein the transfer function to the first and second output signals provide two expressions for the unknown potential signal and the unknown sensor impedance. This circuitry allows a sensor which has first and second unknown impedances which have a known relationship to provide a third expression to determine the two unknown parameters of potential signal and impedance.

In another embodiment the present invention provides a processor for determining a potential signal from first and second amplifier signals, each signal comprising an amplified potential signal received by a sensor electrode at a body and amplified as defined by an operational amplifier with defined feedback impedance and defined series impedances between the sensor receiver and the operational amplifier wherein the processor is operable to determine a potential signal from the first and second amplified signals and, the potential signal determined dependent on an expression for the potential signal which depends on the first and second amplified signals,
feedback component values for first and second amplifier circuits and series impedance values of components at the inputs of the first and second operational amplifiers.

The potential signal may be a biopotential signal.

The body may be a body of a biological organism.

A sensing device for sensing a biopotential signal in a sensing region at a surface of a body the device comprising first and second sensors each comprising an electrode to provide a connection with the body to receive the biopotential signal, wherein the second sensor is arranged to have a connection with the body which has an impedance which is approximately a factor of an impedance of the first sensor with the body.

The electrodes of one or more of the first and second sensors may be operable to form a capacitive connection with the body to receive the biopotential signal.

The second sensor may be operable to form a capacitance with the body which is approximately a factor of the capacitance formed by the first electrode with the body.

The sensing device may comprise a sensing circuit which provides a charge amplifier function for a signal at each sensor, each charge amplification function defined by a series impedance connected in series with the respective sensor and a feedback impedance connected between the series impedance and an output of the circuit.

The sensing circuit may comprise a charge amplifier having one or more feedback components connected between an output terminal and an input terminal of an operational amplifier device.

The one or more feedback components feedback components of the charge amplifier may provide a capacitance and a resistance.

The capacitance provided by the feedback components may be in parallel with the resistance.

The charge amplifier may comprise one or more series components to provide a series impedance between the one or more sensor electrodes and the charge amplifier.

The feedback components may be selected such that for a given series impedance the charge amplifier device provides a gain for a signal into the series impedance which provides a signal-to-noise ratio for the signal into the series impedance compared to electromagnetic background noise which is greater than 0 dB.

The feedback components may be selected such that for a given series impedance and an assumed impedance formed by a sensor electrode and the body the charge amplifier device provides a gain for the biopotential signal which provides a signal-to-noise ratio for the biopotential signal compared to electromagnetic background noise which is greater than 0 dB.

The feedback components may be selected such that for a given series impedance and an assumed impedance formed by a sensor electrode and the body the charge amplifier device has an upper frequency of a pass band which is above a frequency range of the biopotential signal which the sensing device is operable to sense.

The feedback components may be selected such that the charge amplifier device has a lower frequency of a pass band which is below a frequency range of the biopotential signal which the sensing device is operable to sense.

The feedback components and series components may be selected such that for an assumed impedance formed by a sensor electrode and the body the charge amplifier device has an upper corner frequency of a pass band which is above an upper frequency of the biopotential signal which the sensing device is operable to sense.

The feedback components and series components may be selected such that the charge amplifier device has a lower corner frequency of a pass band which is below the frequency range of the biopotential signal which the sensing device is operable to sense.

The feedback components may be selected such that the biopotential signal of a given frequency range is integrated by the charge amplifying device.

The feedback components and/or the series components may be selected so as to provide a series resistance ($R_s$), feedback resistance ($R_f$) and feedback capacitance $C_f$ selected such that $R_f \times C_f > R_s \times C_f$.

The components may be selected such that ratio of unknown capacitances defined by the relation does not equal the ratio of series capacitances at the inputs to the sensing circuitry.

The series components may be selected such that the biopotential signal of a given frequency range is differentiated.

The series components may provide a series capacitance of approximately 22 picofarads or more.

The series components may provide a series capacitance of approximately 500 picofarads or less.

The series components may provide a series capacitance of approximately 100 picofarads or more.

The series components may be selected such that the impedance of the series components is greater than the impedance formed by the sensor and the body alone.

The charge amplifier device may provide an output signal for each sensor electrode.

The sensing device may be operable to sense a biopotential signal with frequencies above approximately 0.1 Hz.

The sensing device may be operable to sense a biopotential signal with frequencies approximately 0.5 Hz and above.

The sensing device may be operable to sense a biopotential signal with frequencies below approximately 1 kHz.

The sensing device may be operable to sense a biopotential signal with frequencies approximately 150 Hz and below.

The applicant has observed that if the impedance of the second electrode is equated to the said relationship of impedance of the second electrode then the impedance of the first sensor can be eliminated from an expression for the biopotential sensed at both sensors wherein the biopotential can be determined dependent on the two charge amplifier outputs, feedback impedances and series impedances.

The sensing device may comprise a processor operable to determine the biopotential signal dependent on biopotential expression derived from expressions for the biopotential sensed via each sensor where the impedance of the second sensor with the body is substituted for the product of the impedance of the first sensor and said impedance factor wherein the bipotential sensed at the second sensor is treated as the biopotential at the first sensor.

The expression used to determine the biopotential signal from charge amplifier outputs may be independent of the impedance at the first sensor wherein the biopotential signal can be determined with an unknown impedance of the first sensor.

The sensor may have one or more electrodes dimensioned such that a connection of the second sensor with the body for the biopotential signal has an impedance which is approximately a factor of the impedance of the first electrode with the body.

The capacitive sensor may have two or more electrodes arranged to provide first and second capacitive signal connections which each have an impedance which differ from each other by a defined relationship. In some embodiments it the capacitive link that is arranged to differ for the two electrodes by the defined relationship. This may be as opposed to resistance, for example, in the electrode itself. This may also be as opposed as opposed to a parasitic capacitance of the electrode or a capacitance or resistance which is connected in parallel with the electrode. In these embodiments the impedance of each capacitive signal connection provided by a respective electrode may be referred to as a first or second sensor impedance. For example, a sensor impedance may be defined predominantly by the capacitance formed between an electrode and skin of the body separated by air or other dielectric material. The sensor impedances may also be referred to as first and second signal-connection impedances. For example, an impedance of a capacitance formed between a second electrode and skin of a body may be a factor, fraction or defined relationship of an impedance of a capacitance formed between a first electrode and skin of the body.

The capacitive sensor may have one or more dielectric layers which, relative one or more dielectric elements of the first capacitive sensor, provide a capacitive connection of the second sensor with the body which has an impedance which is approximately a factor of the impedance of the first capacitive sensor with the body.

One or more electrodes of the second capacitive sensor may be arranged co-axial with the one or more electrodes of the electrode of the first capacitive element.

One or more electrodes of the second capacitive sensor may be arranged to have an area which has a defined relationship to the area of one or more electrodes of the first capacitive element.

One or more electrodes of the second capacitive sensor may be arranged to have a dielectric layer over the electrode which has a permittivity which has a defined relationship to the permittivity of a dielectric layer over one or more electrodes of the first capacitive element.

The defined relationship in permittivity may be arranged by thickness of dielectric material.

The defined relationship in permittivity may be arranged by type of dielectric material.

A sensor may be operable to provide an electrically conductive connection with a surface of the body to receive the biopotential signal. The sensor may comprise a sensor receiver which has a first electrode and a second electrode wherein the second electrode is operable to provide a connection having an impedance which has a defined relationship with a connection provided by the first electrode. The defined relationship of impedances may be arranged by second and/or first electrodes which form differential contact with the surface of the body.

A sensing device for sensing a biopotential signal in a sensing region at a surface of a body the device comprising first and second capacitive sensors each comprising a capacitive electrode to provide a capacitive connection with the body, wherein the second capacitive sensor is arranged to have a capacitive connection with the body with a capacitance which is approximately a factor of a capacitance of the first capacitive sensor with the body.

The capacitive sensor may have one or more electrode dimensions which, relative to dimensions of the electrode of the first capacitive sensor, provide a capacitive signal connection of the second sensor with the body which has a capacitance with the body which is approximately a factor of the capacitance of the first capacitive sensor with the body.

The capacitive sensor may have one or more dielectric layers which, relative one or more dielectric elements of the first capacitive sensor, provide a capacitive connection of the second sensor with the body which has a capacitance with the body which is approximately a factor of the capacitance of the first capacitive sensor with the body.

One or more electrodes of the second capacitive sensor may be arranged co-axial with the one or more electrodes of the electrode of the first capacitive element.

One or more electrodes of the second capacitive sensor may be interleaved with the one or more electrodes of the electrode of the first capacitive element.

Embodiments of the invention provide a process for reconstructing a biopotential signal from first and second sensing signals output by sensing circuitry which receives first and second electrode signals from first and second sensor electrodes which each form a connection for the biopotential signal, the process comprising the steps of:

reading first and second sensor signals;

reading data carrying information which defines an expression for the biopotential signal, the expression derived from i) a first channel expression for the first sensor signal dependent on parameter values for the sensing circuitry providing the first sensor signal, dependent on the impedance formed by the first electrode and dependent on the biopotential signal, and ii) a second channel expression for the second sensor signal dependent on parameter values for the sensing circuitry providing the second sensor signal, dependent on the impedance formed by the second electrode and dependent on the biopotential signal, and iii) an expression for the impedance formed by the second electrode dependent on the impedance formed by the first electrode, wherein the expression is derived to eliminate the impedance formed by the first electrode and eliminate the impedance formed by the second electrode; and determining the bio-potential signal using said expression for the biopotential signal to reconstruct the biopotential signal independently of the first and second impedance.

The expression for the biopotential signal may be the expression below solved for the biopotential, Vin:

$$\begin{pmatrix} TF_{1v} & -i_{u1}TF_{1v} \\ TF_{2v} & -H_{12}i_{u2}TF_{2v} \end{pmatrix} \cdot \begin{pmatrix} V_{in} \\ Z_{u1} \end{pmatrix} = \begin{pmatrix} V_1 & -i_{u1}TF_{1i} \\ V_2 & -i_{u2}TF_{2i} \end{pmatrix}$$

where $TF_{1v}$ is the transfer function between the first sensor electrode voltage and the first sensing signal output, $TF_{1i}$ is the transfer function between the first sensor input current and first sensing signal output, $TF_{2v}$ is the transfer function between the second sensor electrode and the second sensing signal, $TF_{2i}$ is the transfer function between the second sensor input current and second sensing signal output, $i_{u1}$ is the current through the first sensor electrode, $i_{u2}$ is the current through the second sensor electrode, $Z_{u1}$ is the unknown impedance formed by the first sensor electrode and the body, $V_{in}$ is the biopotential signal, $V_1$ is the first sensor signal, $V_2$ is the second sensor signal and $H_{12}$ is a relationship between the first unknown impedance and the second unknown impedance $Z_{u2}$ such that $$Z_{u2} = H_{12}Z_{u1}$$

It is to be understood that the present invention is not limited to the embodiments described herein and further and additional embodiments within the spirit and scope of the invention will be apparent to the skilled reader from the examples illustrated with reference to the drawings. In particular, the invention may reside in any combination of features described herein, or may reside in alternative embodiments or combinations of these features with known equivalents to given features. Modifications and variations of the example embodiments of the invention discussed above will be apparent to those skilled in the art and may be made without departure of the scope of the invention as defined in the appended claims.

What we claim is:

1. An apparatus operable to reconstruct a biopotential signal from a signal received at a surface of a body, the apparatus comprising:
a sensor device which forms a first signal connection for the biopotential signal, the first signal connection having a first sensor impedance, and which forms a second signal connection for the biopotential signal, the second signal connection having a second sensor impedance, wherein the sensor device is arranged such that the second sensor impedance is linearly related to the first sensor impedance by an impedance relation;
sensor circuitry which provides i) a first sensor signal related to the biopotential signal by a first channel expression which is dependent on parameter values for the sensing circuitry providing the first sensor signal, dependent on the first sensor impedance and dependent on the biopotential signal, and ii) a second sensor signal related to the biopotential signal by a second channel expression which is dependent on parameter values for the sensing circuitry, dependent on the second sensor impedance and dependent on the biopotential signal;
a processor operable to read data carrying information on parameter values of the receiver circuitry, operable to read data carrying information on the first sensor signal, operable to read data carrying information on the second sensor signal and operable to generate data carrying information on a reconstruction of the biopotential signal said reconstruction using a derived biopotential relation which is derived from a set of relations comprising the first channel expression, the second channel expression and the impedance relation, wherein the derived biopotential relation used to reconstruct the biopotential signal is independent of the first sensor impedance.

2. The apparatus of claim 1 wherein a channel expression defines a transfer function.

3. The apparatus of claim 2 wherein the transfer function of the first channel comprises an analytic relation for the gain of a first channel comprising at least one of a relation to the current entering the first channel and a relation to the voltage signal at the entry of the first channel, and wherein the transfer function of the second channel comprises an analytic relation for the gain of a second channel comprising at least one of a relation for the current entering the second channel and a relation to the signal at the entry of the second channel.

4. The apparatus of claim 2 wherein a first channel transfer function comprises an analytic relation for the gain of a first channel comprising an operational amplifier circuit having a selected feedback impedance a selected series impedance connected at an input of an operational amplifier and comprising an impedance in series with the selected series impedance to represent the first sensor impedance, and wherein the second channel transfer function of the second channel comprises an analytic relation for the gain of a second channel comprising an operational amplifier circuit having a selected feedback impedance a selected series impedance connected at an input of an operational amplifier and comprising an impedance in series with the selected series impedance to represent the second sensor impedance.

5. The apparatus of claim 2, wherein the transfer function of the first channel comprises:

$$V_1 = -\frac{Z_{f1}}{Z_{s1} + Z_{u1}} V_{in}$$

where $V_1$ is the output of the first channel, $V_{in}$ is the bipotential signal $Z_{f1}$ is a selected first channel feedback impedance, $Z_{s1}$ is a selected first channel series impedance and $Z_{u1}$, is the first sensor impedance and the transfer function of the second channel comprises:

$$V_2 = -\frac{Z_{f2}}{Z_{s2} + H_{12}Z_{u1} + k_{12}} V_{in}$$

where $V_2$ is the output of the second channel, $Z_{f2}$ is a selected second channel feedback impedance, $Z_{s2}$ is a selected second channel series impedance $Z_{u2}$ is the second sensor impedance, $H_{12}$ defines a relationship between the first sensor impedance and the second sensor impedance $Z_{u2}$ such that $Z_{u2}=H_{12}Z_{u1}$
and wherein the biopotential signal is reconstructed using the relation $$V_{in} = \frac{V_1 V_2 (k_{12} + H_{12} Z_{s1} - Z_{s2})}{-H_{12} V_2 Z_{f1} + V_1 Z_{f2}}.$$

6. The apparatus of claim 2 wherein the transfer function of each of a multiplicity of n signal channels comprises:

$$V_n = i_{un}TF_{ni} + V_{in}TF_{nv} + i_{un}Z_{un}TF_{nv}$$

and wherein the relation between the unknown first impedance parameter and unknown second impedance parameter comprises $$Z_{un} = H_{1n} Z_{u1}$$

and the captured biopotential signal is determined by the processor using $$\begin{pmatrix} V_{in} \\ Z_{u1} \end{pmatrix} = \begin{pmatrix} TF_{1v} & i_{u1}TF_{1v} \\ TF_{2v} & H_{12}i_{u2}TF_{2v} \\ \vdots & \vdots \\ TF_{nv} & H_{1n}i_{un}TF_{nv} \end{pmatrix}^+ \begin{pmatrix} V_1 - i_{u1}TF_{1i} \\ V_2 - i_{u2}TF_{2i} - i_{u2}k_{12}TF_{2v} \\ \vdots \\ V_n - i_{un}TF_{ni} - i_{un}k_{1n}TF_{nv} \end{pmatrix}$$

where $A^+$ represents an operator such that if A x=b, x=A+b where $Z_{u2}$ is the second sensor impedance $Z_{u2}$ is the first sensor impedance, $H_{1n}$ is a factor and $k_{12}$ is a constant, and where $TF_{nv}$ a transfer function.

7. The apparatus of claim 1, wherein the sensor circuitry provides a first channel and the first channel expression is:

$$V_1 = i_{u1}TF_{1i} + V_{in}TF_{1v} + i_{u1}Z_{u1}TF_{1v}$$

where $i_{u1}$ is the current entering the channel, $V_{in}$ is the signal at the entry of the first channel, $V_1$ is the output of the first signal channel, $Z_{u1}$ is the first sensor impedance, $TF_{1i}$ is the relation for the gain for the current entering the first channel, $TF_{1v}$ is a relation for the gain for the signal at the entry of the first channel, and wherein the sensor circuitry provides a second channel and the second channel expression is:

$$V_2 = i_{u2}TF_{2i} + V_{in}TF_{2v} + i_{u2}Z_{u2}TF_{2v}$$

where $i_{u2}$ is the current entering the channel, $V_{in}$ is the signal at the entry of the channel, $V_2$ is the output of the second signal channel, $Z_{u2}$ is the unknown second impedance, $TF_{2i}$ is the relation for the gain to the current entering the second channel, $TF_{2v}$ is the relation for the gain for the signal at the entry of the channel.

8. The apparatus of claim 7 wherein the first signal channel comprises the first signal connection in series with sensor circuitry which is arranged so that the first channel transfer function is non-linearly related to the first sensor impedance.

9. The apparatus of 1 wherein the impedance relation is:

$$Z_{u2} = H_{12}Z_{u1} + k_{12}$$

where $Z_{u2}$ is the second sensor impedance $Z_{u2}$ is the first sensor impedance, $H_{12}$ is a factor and $k_{12}$ is a constant.

10. The apparatus of claim 9, wherein the derived biopotential relation used by the processor is:

$$V_{in} = \frac{H_{12}i_{u2}(-V_1 + i_{u1}TF_{1i})TF_{2v} + i_{u1}TF_{1v}(V_2 - i_{u2}TF_{2i} - i_{u2}k_{12}TF_{2v})}{(i_{u1} - H_{12}i_{u2})TF_{1v}TF_{2v}}$$

where $i_{u1}$ is a current entering the first channel and $i_{u2}$ entering the second channel, $i_{u1}$ is the current entering the channel, $V_{in}$ is the signal at the entry of the first channel, $V_1$ is the output of the first signal channel, $Z_{u1}$ is the first sensor impedance, $TF_{1i}$ is the relation for the gain for the current entering the first channel, $TF_{1v}$ is a relation for the gain for the signal at the entry of the first channel, where $i_{u2}$ is the current entering the channel, $V_{in}$ is the signal at the entry of the channel, $V_2$ is the output of the second signal channel, $Z_{u2}$ is the unknown second impedance, $TF_{2i}$ is the relation for the gain to the current entering the second channel, $TF_{2v}$ is the relation for the gain for the signal at the entry of the channel, and where $Z_{u2}$ is the second sensor impedance $Z_{u2}$ is the first sensor impedance, $H_{12}$ is a factor and $k_{12}$ is a constant.

11. The apparatus of claim 1 wherein the processor is operable to generate data carrying information on an estimate of the unknown first impedance using the relation:

$$Z_{u1} = \frac{(V_1 - i_{u1}TF_{1i})TF_{2v} + TF_{1v}(-V_2 + i_{u2}TF_{2i} + i_{u2}k_{12}TF_{2v})}{(i_{u1} - H_{12}i_{u2})TF_{1v}TF_{2v}}$$

where $i_{u1}$ is a current entering the first channel and $i_{u2}$ entering the second channel, $i_{u1}$ is the current entering the channel, $V_{in}$ is the signal at the entry of the first channel, $V_1$ is the output of the first signal channel, $Z_{u1}$ is the first sensor impedance, $TF_{1i}$ is the relation for the gain for the current entering the first channel, $TF_{1v}$ is a relation for the gain for the signal at the entry of the first channel, where $i_{u2}$ is the current entering the channel, $V_{in}$ is the signal at the entry of the channel, $V_2$ is the output of the second signal channel, $Z_{u2}$ is the unknown second impedance, $TF_{2i}$ is the relation for the gain to the current entering the second channel, $TF_{2v}$ is the relation for the gain for the signal at the entry of the channel, and where $Z_{u2}$ is the second sensor impedance $Z_{u2}$ is the first sensor impedance, $H_{12}$ is a factor and $k_{12}$ is a constant.

12. The apparatus of claim 1 wherein the receiver circuitry is operable to output a first current measurement $i_{u1}$ of a current entering the first channel and a second current measurement $i_{u2}$ entering the second channel.

13. The apparatus of claim 1 wherein the receiver circuitry comprises a first receiver circuit having a transfer function defined by a first feedback impedance and a first series impedance, wherein the first receiver circuit is a charge amplifier, and wherein the charge amplifier is an inverting amplifier with a feedback impedance between an output and an inverting input and a series impedance at the inverting input.

14. The apparatus of claim 1, wherein the biopotential signal, outputs of the receiver circuitry and sensor impedances are defined in the frequency domain and wherein the processor operates in the frequency domain.

15. The apparatus of claim 1, wherein the first channel expression comprises:

$$V_1 = \left(1 + \frac{Z_{f1}}{Z_1}\right)V_{in}$$

where $V_1$ is the output of the first channel, $V_{in}$ is the biopotential signal $Z_1$ is the first sensor impedance, $Z_{s1}$ is a selected first channel series impedance and wherein the second channel expression comprises $$V_2 = \left(1 + \frac{Z_{f2}}{Z_2}\right)V_{in}$$

where $V_2$ is the output of the second channel, $Z_2$ is the second sensor impedance, $Z_{f2}$ is a selected second channel feedback impedance and wherein the biopotential signal is reconstructed using:

$$V_{in} = \frac{V_2 Z_2}{Z_2 + Z_{f2}}.$$

16. The apparatus of claim 1 wherein, wherein the first channel expression comprises:

$$V_1 = \left(1 + \frac{Z_{f1}}{Z_1}\right)V_{in}$$

where $Z_1$ the first signal impedance signal connection and the transfer function of the second channel comprises $$V_2 = \left(1 + \frac{Z_{f2}}{Z_2}\right)V_{in}$$

where $Z_2$ is the second impedance signal and where the derived expression is $$V_{in} = \frac{i_{u1}V_2Z_2(Z_1 + Z_{f1}) - H_{12}i_{u2}V_1Z_1(Z_2 + Z_{f2})}{(i_{u1} - H_{12}i_{u2})(Z_1 + Z_{f1})(Z_2 + Z_{f2})}$$

where $i_{u1}$ is the current entering the first input channel and $i_{u2}$ is the current entering the second input channel.

17. The apparatus of claim 1, wherein the first channel expression comprises:

$$V_1 = \frac{Z_{41}}{Z_{21} + Z_{41}} \frac{(Z_{11} + Z_{31})}{Z_{11}} V_{in}$$

where $Z_{11}$, $Z_{21}$, $Z_{31}$ and $Z_{41}$ are impedance parameters of the first signal channel, and the second channel expression comprises:

$$V_2 = \frac{Z_{42}}{Z_{22} + Z_{42}} \frac{(Z_{12} + Z_{32})}{Z_{12}} V_{in}$$

where $Z_{12}$, $Z_{22}$, $Z_{32}$ and $Z_{42}$ are impedance parameters of the first signal channel, and where the captured biopotential signal is determined from:

$$V_{in} = \frac{V_1 V_2 Z_{11} Z_{12}(Z_{22}Z_{41} + (Z_{41} - H_{12}(Z_{21} + Z_{41}))Z_{42})}{(-H_{12}V_2Z_{12}(Z_{11} + Z_{31}) + V_1Z_{11}(Z_{12} + Z_{32}))Z_{41}Z_{42}}.$$

18. The apparatus of claim 1, wherein the sensor device comprises one or more electrodes operable to provide a capacitive connection for the biopotential signal at the surface of the body.

19. The apparatus of claim 1, wherein the sensor device comprises one or more electrodes operable to provide a conductive connection for the biopotential signal at the surface of the body.

20. The apparatus of claim 1, wherein the sensor device has an electrode common to first and second signal connections.

21. A process of capturing a biopotential signal at a surface of a body using a sensor receiver which forms a first signal connection with the body wherein one or more parameters of impedance of the first signal connection are unknown, the process comprising:
receiving the biopotential signal at an output of a first signal channel having a first channel transfer function which is dependent on the one or more unknown first impedance parameters;
receiving the biopotential signal at an output of one or more second signal channels each having a second channel transfer function dependent on the one or more unknown first impedance parameters;
solving a set of relations to determine the captured biopotential signal independently of the unknown one or more impedance parameters of the first signal connection, wherein the set of relations is defined dependent on:
i) the first channel transfer function,
ii) the second channel transfer function, and
iii) outputs of the first and second signal channels, and
wherein the second channel transfer function is dependent on the first unknown impedance parameter by being dependent on a second impedance parameter which has a known relation to the unknown first impedance parameter.

22. The process of claim 21, wherein the solved set of relations comprises a first relation which relates the biopotential signal to an expression which is dependent on the output signal of the first signal channel, the unknown first impedance parameter and one or more known parameters for components included in the first signal channel.

* * * * *